(12) United States Patent
Jackson et al.

(10) Patent No.: US 10,053,476 B2
(45) Date of Patent: Aug. 21, 2018

(54) PHOSPHOHISTIDINE AND PHOSPHOTYROSINE ANALOGUES

(71) Applicant: UNIVERSITY OF SHEFFIELD, Sheffield (GB)

(72) Inventors: Richard Jackson, Sheffield (GB); Richmond Muimo, Leeds (GB); Matthew Lilley, Sheffield (GB)

(73) Assignee: UNIVERSITY OF SHEFFIELD, Sheffield (GB)

( * ) Notice: Subject to any disclaimer, the term of this patent is extended or adjusted under 35 U.S.C. 154(b) by 0 days.

(21) Appl. No.: 14/914,994

(22) PCT Filed: Sep. 2, 2014

(86) PCT No.: PCT/GB2014/052646
§ 371 (c)(1),
(2) Date: Feb. 26, 2016

(87) PCT Pub. No.: WO2015/033120
PCT Pub. Date: Mar. 12, 2015

(65) Prior Publication Data
US 2016/0207948 A1    Jul. 21, 2016

(30) Foreign Application Priority Data

Sep. 4, 2013 (GB) .................. 1315751.6

(51) Int. Cl.
| | | |
|---|---|---|
| *A61K 39/385* | (2006.01) | |
| *C07F 9/6503* | (2006.01) | |
| *C07F 9/6539* | (2006.01) | |
| *C07K 16/44* | (2006.01) | |
| *G01N 33/53* | (2006.01) | |
| *C07F 9/58* | (2006.01) | |
| *C07F 9/6553* | (2006.01) | |
| *C07K 14/00* | (2006.01) | |

(52) U.S. Cl.
CPC .......... *C07F 9/65036* (2013.01); *C07F 9/587* (2013.01); *C07F 9/6539* (2013.01); *C07F 9/655345* (2013.01); *C07K 14/001* (2013.01); *C07K 16/44* (2013.01); *G01N 33/5308* (2013.01); *G01N 2440/14* (2013.01)

(58) Field of Classification Search
CPC .... C07F 9/587; C07F 9/65036; C07F 9/6539; C07F 9/655345; C07K 16/44; C07K 14/001; G01N 33/5308; G01N 2440/14; G01N 33/53; A61K 39/385
See application file for complete search history.

(56) References Cited

U.S. PATENT DOCUMENTS

2015/0004173 A1 * 1/2015 Stankova ............... C07K 16/40
424/139.1

FOREIGN PATENT DOCUMENTS

| WO | 2012040523 A2 | 3/2012 |
| WO | 2013138474 A1 | 9/2013 |
| WO | 2015051079 A2 | 4/2015 |

OTHER PUBLICATIONS

Supporting Information for: Kee et al., "A second-generation phosphohistidine analog for production of phosphohistidine antibodies." Org Lett. 17(2): 187-9,15 pages (2015).
Supporting Information for: Kee et al., "A pan-specific antibody for direct detection of protein histidine phosphorylation," Nat Chem Biol. 9(7): 416-21, 51 pages (2013). Retrieved from: <nature.com/nchembio/journal/v9/n7/extref/nchembio.1259-S1.pdf> last accessed on Sep. 12, 2016.
Frackelton, A. Raymond, et al., Characterization and Use of Monoclonal Antibodies for Isolation of Phosphotyrosyl Proteins from Retrovirus-Transformed Cells and Growth Factor-Stimulated Cells, Molecular and Cellular Biology, 3(8):1343-1352, Aug. 1983.
Arad-Dann, Hadas, et al., Immunohistochemistry of Phosphotyrosine Residues: Identification of Distinct Intracellular Patterns in Epithelial and Steroidogenic Tissues, The Journal of Histochemistry and Cytochemistry, 41(4):513-519, 1993.
Yan, Jun X., et al., Protein phosphorylation: technologies for the identification of phosphoamino acids, 808:23-41, Journal of Chromatography 1998.
Kee, Jung-Min, et al., Development of Stable Phosphohistidine Analogues, J. Am. Chem. Soc., 132:14327-14329, 2010.
McAllister, Tom E., et al., Fmoc-chemistry of a stable phosphohistidine analogue, Chem. Commun., 47:1297-1299, 2011.
Mukai, Shin, et al., Stable triazolylphosphonate analogues of phosphohistidine, Amino Acids, 43;857-874, 2012.
Eerland, Martijn, et al., Design and Synthesis of an Fmoc-SPPS-Compatible Amino Acid Building Block Mimicking the Transition State of Phosphohistidine Phosphatase, J. Org. Chem., 77:2047-2052, 2012.
McAllister, Tom E., Triazole phosphohistidine analogues compatible with the Fmoc-strategy, Org. Biomol. Chem., 10:4043-4049, 2012.
McAllister, Tom E., et al., Prospects for stable analogues of phosphohistidine, Biochem. Soc. Trans., 41:1072-1077, 2013.

(Continued)

*Primary Examiner* — Shafiqul Haq
(74) *Attorney, Agent, or Firm* — McCarter & English, LLP; Steven G. Davis; Joshua J. Galgano

(57) ABSTRACT

The invention relates to phosphohistidine analogs. The invention also relates to antibodies that specifically bind to the analogs and methods of generating said antibodies. In one embodiment of the invention there is provided a phosphohistidine analog of Formula V: (V) wherein W is selected from H, $CO_2H$ or $CONH_2$; and X is selected from CH or N.

Formula V

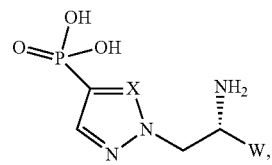

12 Claims, 11 Drawing Sheets

(56) References Cited

OTHER PUBLICATIONS

Kee, Jung-Min, et al., A pan-specific antibody for direct detection of protein histidine phosphorylation, Nature Chemical Biology, 9:416-421, Jul. 2013.
McAllister, Tom E., et al., Evaluation of the Interaction between Phosphohistidine Analogues and Phosphotyrosine Binding Domains, ChemBioChem, 15:1088-1091, 2014.
Lilley, Matthew, et al., 4-Phosphothiophen-2-yl alanine: a new 5-membered analogue of phosphotyrosine, Chem. Commun. 50:9343-9345, 2014.
Oslund, Rob C., et al., A Phosphohistidine Proteomics Strategy Based on Elucidation of a Unique Gas-Phase Phosphopeptide Fragmentation Mechanism, J. Am. Chem. Soc., 136:12899-12911, 2014.
Fuhs, Stephen Rush, et al., Monoclonal 1- and 3-Phosphohistidine Antibodies: New Tools to Study Histidine Phosphorylation, Cell, 162:198-210, Jul. 2, 2015.
Lilley, Matthew, et al., 4-Phosphopyrazol-2-yl alanine: a non-hydrolysable analogue of phosphohistidine, Chem. Commun., 51:7305-7308; 2015.
Kee, Jung-Min, et al., A Second-Generation Phosphohistidine Analog for Production of Phosphohistidine Antibodies, Org. Let, 17:187-189: 2015.
STN Reg, RN# 933733-97-2, Apr. 30, 2007.
Mukai, Shin, PhD Thesis, Stable Analogues of Phosphohistidine, University of Western Australia, Apr. 2011.
Cherney et al., Efficient Mitsunobu Reactions with N-Phenylfluorenyl or N-Trityl Serine Esters. J Org Chem. 1996;61: 2544-2546.
Krenk et al., Methodology for Synthesis of Enantiopure 3,5-Disubstituted Pyrrole-2-ones. Eur J Org Chem. 2015: 5414-5423.
Tsunoda et al., 1,1'(Azodicarbonyl)dipiperidine-Tributylphosphine, A New Reagent System for Mitsunobu Reaction. Tetrahedron Letters. 1993;34(10):1639-1642.
Tsunoda et al., Mitsunobu Acylation of Sterically Congested Secondary Alcohols by N,N,N',N'-Tetramethylazodicarboxamide-Tributylphosphine Reagents. Tetrahedron Letters. 1995;36(14):2529-2530.
Zwanenburg, Synthetic potential of heteroatomic ring systems. Pure Appl Chem. 1999;71(3):423-430.

* cited by examiner

|   | Histidine | | pHistidine | | pSerine | | pThreonine | | pTyrosine | | Controls | |
|---|---|---|---|---|---|---|---|---|---|---|---|---|
|   | 1 | 2 | 3 | 4 | 5 | 6 | 7 | 8 | 9 | 10 | 11 | 12 |
| a | 5.00 | | 5.00 | | 5.00 | | 5.00 | | 5.00 | | 0 | |
| b | 2.50 | | 2.50 | | 2.50 | | 2.50 | | 2.50 | | Blocked | |
| c | 1.25 | | 1.25 | | 1.25 | | 1.25 | | 1.25 | | Primary | |
| d | 0.63 | | 0.63 | | 0.63 | | 0.63 | | 0.63 | | Secondary | |
| e | 0.32 | | 0.32 | | 0.32 | | 0.32 | | 0.32 | | | |
| f | 0.16 | | 0.16 | | 0.16 | | 0.16 | | 0.16 | | | |
| g | 0.08 | | 0.08 | | 0.08 | | 0.08 | | 0.08 | | | |
| h | 0.04 | | 0.04 | | 0.04 | | 0.04 | | 0.04 | | | |

Figure 10

PHOSPHOHISTIDINE AND PHOSPHOTYROSINE ANALOGUES

RELATED APPLICATIONS

This application is a 35 U.S.C. § 371 national stage filing of International Application No. PCT/GB2014/052646, filed on Sep. 2, 2014, which claims the benefit of United Kingdom Patent Application No. 1315751.6, filed on Sep. 4, 2013, each of which are hereby incorporated herein by reference in their entirety.

This invention relates to phosphohistidine and phosphotyrosine analogues. The invention also relates to antibodies that specifically bind to the analogues and methods of generating said antibodies.

BACKGROUND

Phosphorylation is a major signalling mechanism involved in cellular protein regulation. Phospho-specific antibodies that can specifically discriminate between phosphorylated and non-phosphorylated forms of a polypeptide have emerged as key tools for analysis of phosphorylation.

A number of proteins are phosphorylated on histidine, such as NDPK, ATP citrate lyase, the G-protein Gβ subunit, and the potassium channel, KCa3.1, P-selectin and annexin 1. Moreover, these phosphorylation events are linked to a number of diseases including cancer, cardiovascular defects, inflammation and diabetes.

Even though it is believed that 6% of all mammalian phosphorylations occur on histidine, the instability and relative low abundance of phosphohistidine in comparison to phosphoserine and phosphothreonine has made it difficult to study. Similar problems were observed during early studies of phosphotyrosine, due to its relatively low abundance and its instability. However antibodies specific for phosphotyrosine have been developed, allowing the detection of phosphotyrosine residues using immunofluorescence, and for immunoaffinity concentration of the phosphoproteins prior to digestion and mass spectrometric peptide analysis.

The difficulties associated with detection of phosphohistidine residues have led to a number of approaches and techniques in order to understand phosphorylation dynamics of proteins.

The traditional approach of using Edman degradation as a way to identify phosphohistidine residues is possible. However, this approach is not without its limitations as the percentage of protein phosphorylated on phosphohistidine is naturally low, as well as instability of the phosphoramidate bond leading to further decomposition. The acid lability of phosphohistidine is also known to be a limitation in the study of phosphohistidine proteins. Accordingly, the main problem relating to the analysis of phosphohistidine residues is in fact not the detection of the residue, but the techniques used to prepare the samples for analysis. This suggests the main area to concentrate on is the enrichment of complex sample mixtures. In this regard, antibodies appear to have most potential to improve phosphohistidine detection, as they can be utilized in detection and enrichment without the need for acidic conditions.

In recent years a number of phosphospecific antibodies have been developed that can typically detect femtomolar amounts of specific phosphoproteins (Yan, J. X.; Packer, N. H.; Gooley, A. A.; Williams, K. L. J. Chromatogr. A 1998, 808, 23-41). This has led to the development of monoclonal antibodies that recognise phosphoserine, phosphothreonine, and phosphotyrosine residues, via the use of a bovine serum albumin (BSA) or keyhole limpet hemocyanin (KLH) conjugate. Each of these antibodies shows no cross reactivity towards other phosphoamino acids, or the respective non-phosphorylated amino acid, however if the residue of interest is buried within the protein the detection of phosphoamino acids can be hindered (Arad-Dann, H.; Beller, U.; Haimovitch, R.; Gavrieli, Y.; Ben-Sasson, S. A. J. Histochem. Cytochem. 1993, 41, 513-9). This means that the selection of antibody needs to be tested against individual proteins.

For phosphoserine and phosphothreonine the generation of antibodies was relatively simple, the antibodies being made by simply conjugating the residues to KLH or BSA. However, this was not the case for phosphotyrosine and phosphohistidine due to them both being unstable under typical biological conditions. Unlike the more commonly studied phosphohydroxyamino acids (phosphoserine, phosphothreonine and phosphotyrosine), the phosphoryl group in phosphohistidine is attached to a histidine ring, as a phosphoramidate bond, which is acid labile making it unstable under physiological conditions and therefore difficult to study. In view of the fact that phosphohistidine is unstable, it cannot be used successfully to generate antibodies.

Due to ease of hydrolysis of phosphohistidine it has been impossible to generate antibodies directly from the amino acid of interest. This has prompted a number of researchers to attempt to design and synthesise a suitable stable analogue of phosphohistidine.

The first report of an antibody that could detect phosphohistidine was by Frackelton and co-workers; when generating a monoclonal antibody towards phosphotyrosine, some cross reactivity was observed for phosphohistidine (Mol. Cell. Biol., 1983, 1343). The first successful approach that targetted phosphohistidine was reported in 2010 by Muir and co-workers (J. Am. Chem. Soc. 2010, 132, 14327), who used phosphoryltriazolylalanine. The phosphoryltriazolylalanine was incorporated into a peptide sequence found in the "tail end" of Histone H4 as a replacement for a specific histidine residue. The peptide was then used to generate antibodies and tested via dot blot analysis. These results demonstrated a selectivity towards the specifically phosphorylated histidine peptide, however the antisera used did not detect the peptide incorporating a phosphohistidine residue at a different site. In addition, further work in this field by Muir and co-workers in 2013 (Nat. Chem. Bio. 2013, 9, 416-421) involved the development of a phosphoryl-triazolylethylamine based polyclonal antibody able to recognize phosphohistidine. However, this particular antibody exhibited high cross reactivity with phosphotyrosine limiting its useful application.

Accordingly, there remains a need for improved antibodies for specifically detecting phosphohistidine or phosphotyrosine.

BRIEF SUMMARY OF THE DISCLOSURE

In accordance with the present invention there is provided a phosphohistidine analogue of Formula I:

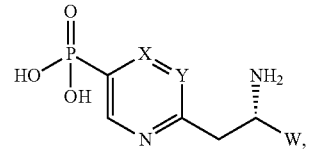

Formula I wherein
X is selected from CH or N;
Y is selected from CH or N; and
W is selected from H, $CO_2H$ or $CONH_2$.

Preferably, W is selected from H or CO$_2$H.

Preferably, the phosphohistidine analogue of Formula I is selected from the group consisting of:

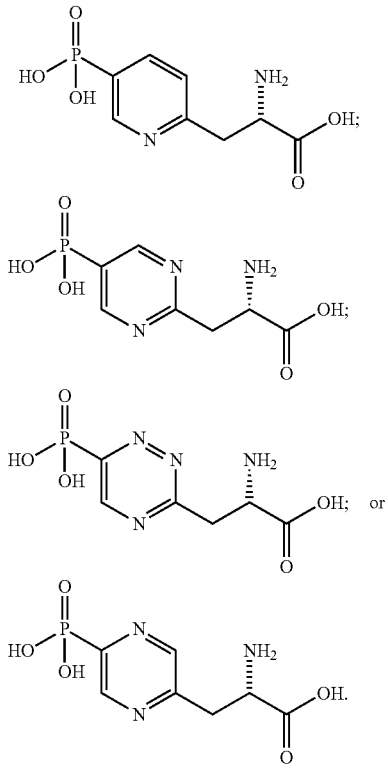

Preferably, the phosphohistidine analogue of Formula I analogue is:

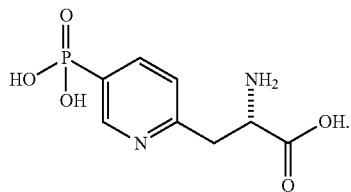 [SMILES: N[C@@H](Cc1ccc(P(=O)(O)O)cn1)C(=O)O]

In a further aspect, there is provided a phosphohistidine analogue of Formula II:

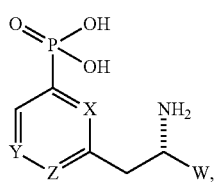

Formula II wherein
X is selected from CH or N;
Y is selected from CH or N;
W is selected from H, CO$_2$H or CONH$_2$; and
Z is selected from CH or N;
with the proviso that at least one of X, Y or Z is selected from N.

Preferably, W is selected from H or CO$_2$H.

Preferably, the phosphohistidine analogue of Formula II is selected from the group consisting of:

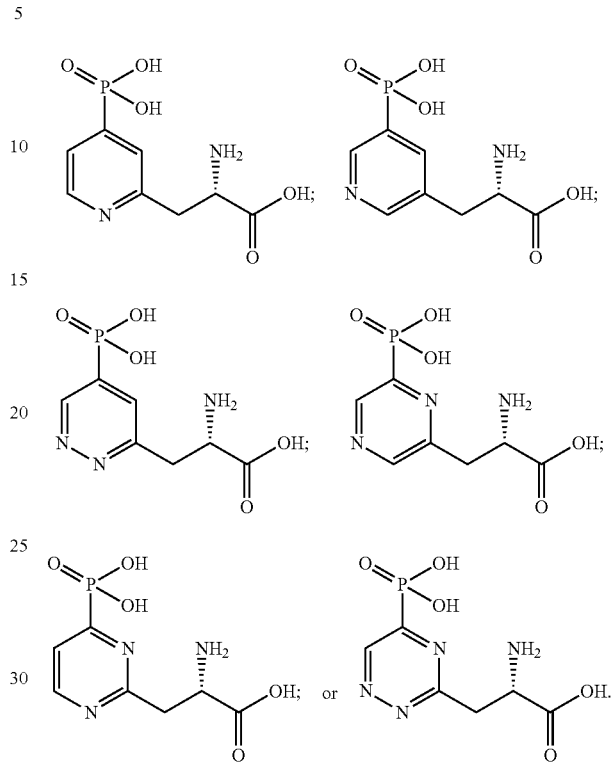

Preferably, the phosphohistidine analogue of Formula II is:

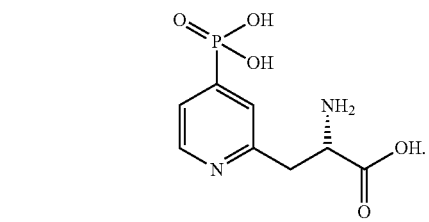

In a further aspect, there is provided a phosphohistidine analogue of Formula III:

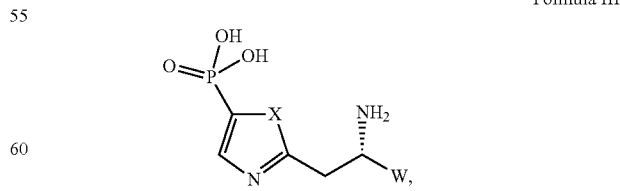

Formula III wherein
W is selected from H, CO$_2$H or CONH$_2$; and
X is selected from NH, O or S.

Preferably, W is selected from H or CO₂H.

Preferably, the phosphohistidine analogue of Formula III is selected from the group consisting of:

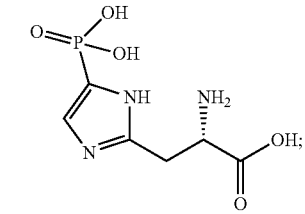

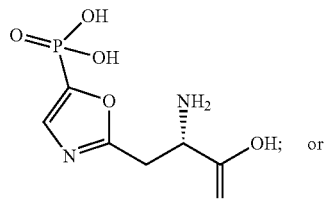   or

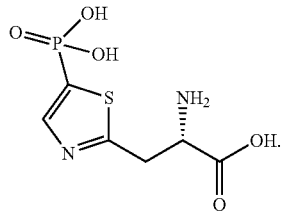

In a further aspect, there is provided a phosphohistidine analogue of Formula IV:

Formula IV

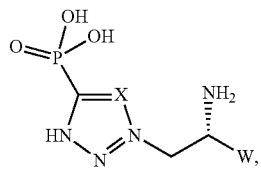

wherein
W is selected from H, CO₂H or CONH₂; and
X is selected from CH or N.

Preferably, W is selected from H or CO₂H.

In a further aspect, there is provided a phosphohistidine analogue of Formula V:

Formula V

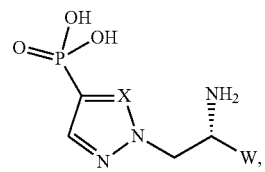

wherein
W is selected from H, CO₂H or CONH₂; and
X is selected from CH or N.

Preferably, W is selected from H or CO₂H.

Preferably, the phosphohistidine analogue of Formula V is:

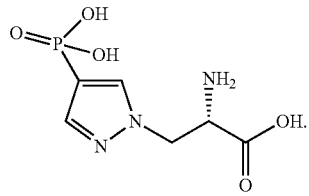 [SMILES: N[C@@H](Cn1cc(P(=O)(O)O)cn1)C(=O)O]

In a further aspect, there is provided a phosphohistidine analogue of Formula VI:

Formula VI

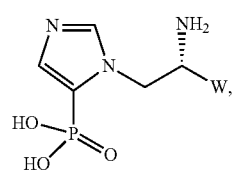

wherein
W is selected from H, CO₂H or CONH₂.

Preferably, W is selected from H or CO₂H.

In a further aspect, there is provided phosphohistidine analogues selected from the group consisting of:

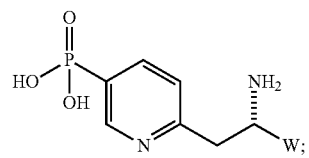

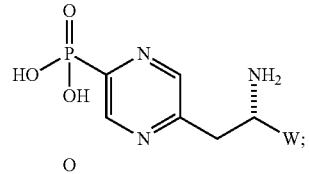

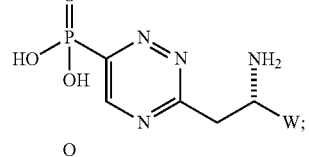

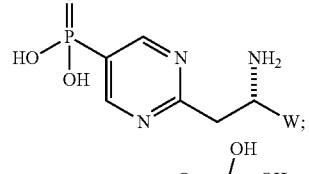

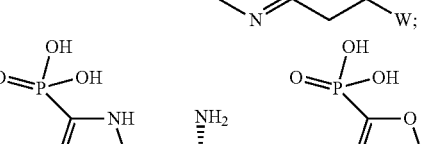

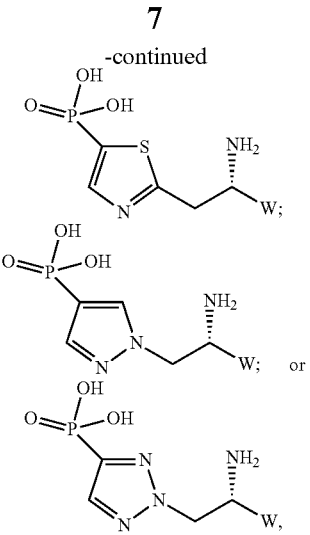

wherein
W is selected from H, $CO_2H$ or $CONH_2$. The aforementioned selected phospohistdine analogues fall within the scope of Formula I, III or V and abide by a common design concept devised to mimic tele-phosphohistidine and maximize their efficacy.

Preferably, W is selected from H or $CO_2H$.

In some preferred embodiments of the phosphohistidine analogues of Formula I, II, III, IV, V and VI, W is selected from $CO_2H$.

In other preferred embodiments of the phosphohistidine analogues of Formula I, II, III, IV, V and VI, W is selected from H.

In further preferred embodiments of the phosphohistidine analogues of Formula I, II, III, IV, V and VI, W is selected from $CONH_2$.

The above-described phosphohistidine analogues of Formula I, II, III, IV and V can provide stable analogues of tele-phosphohistidine.

The above-described phosphohistidine analogues of Formula VI can provide stable analogues of pros-phosphohistidine.

In a further aspect, there is provided a polypeptide comprising any one of the phosphohistidine analogues of Formula I, II, III, IV, V and VI.

In yet a further aspect, there is provided an antibody or fragment thereof, that binds to any one of the phosphohistidine analogues of Formula I, II, III, IV, V and VI.

In one preferred embodiment, said antibody is a polyclonal antibody.

In another preferred embodiment, said antibody is a monoclonal antibody.

Preferably, said antibody specifically binds to a phosphohistidine amino acid residue or analogue thereof.

Preferably, said phosphohistidine amino acid residue is a residue in a polypeptide.

In a further aspect of the present invention there is provided a method of producing an anti-phosphohistidine antibody, comprising:
(a) immunizing a non-human animal with an analogue according to any one of the phosphohistidine analogues of Formula I, II, III, IV, V and VI;
(b) collecting serum from the immunized animal;
(c) isolating from the serum a population of polyclonal antibodies that bind to the analogue.

In one preferred embodiment of said method of producing an anti-phosphohistidine antibody, said analogue is provided as an amino acid residue in a polypeptide.

In another preferred embodiment of said method of producing an anti-phosphohistidine antibody, said analogue is coupled to a carrier protein.

Preferably, said carrier protein is selected from keyhole limpet hemocyanin (KLH), or bovine serum albumin (BSA).

In a further preferred embodiment of said method of producing an anti-phosphohistidine antibody, the binding of said polyclonal antibodies to said analogue is independent of the amino acid sequence of the polypeptide or carrier protein.

In yet a further preferred embodiment of said method of producing an anti-phosphohistidine antibody, the method further comprises a step of enriching the population of polyclonal antibodies that bind to the analogue.

In a further aspect of the present invention there is provided a polyclonal antibody or fragment thereof or a population of polyclonal antibodies obtainable by said method of producing an anti-phosphohistidine antibody.

In yet a further aspect of the present invention there is provided a further method of producing an anti-phosphohistidine antibody, comprising:
(a) immunizing a non-human animal with an analogue according to any one of the phosphohistidine analogues of Formula I, II, III, IV, V and VI;
(b) generating hybridomas by fusing B-cells isolated from the immunized animal with myeloma cells;
(c) identifying hybridomas that produce monoclonal antibodies that bind to the analogue; and
(d) propagating said identified hybridomas to produce monoclonal antibodies that bind to the analogue.

In one preferred embodiment of said further method of producing an anti-phosphohistidine antibody, said analogue is provided as an amino acid residue in a polypeptide.

In another preferred embodiment of said further method of producing an anti-phosphohistidine antibody, said analogue is coupled to a carrier protein.

Preferably, said carrier protein is selected from keyhole limpet hemocyanin (KLH), or bovine serum albumin (BSA).

In a further preferred embodiment of said further method of producing an anti-phosphohistidine antibody the binding of said monoclonal antibodies to said analogue is independent of the amino acid sequence of the polypeptide or carrier protein.

In a further aspect of the present invention there is provided a monoclonal antibody or fragment thereof obtainable by said further method of producing an anti-phosphohistidine antibody.

In a still further aspect of the present invention there is provided a method of detecting a phosphohistidine-containing polypeptide comprising:
(a) containing a test polypeptide with an antibody or fragment thereof, that binds to any one of the phosphohistidine analogues of Formula I, II, III, IV, V and VI or an anti-phosphohistidine antibody as herein described above; and
(b) detecting binding of said antibody to said test polypeptide,
wherein binding of the antibody to the test polypeptide identifies the polypeptide as containing a phosphohistidine residue.

In a yet still further aspect of the present invention this is provided the use of an antibody or fragment thereof as herein described above to identify a phosphohistidine residue or a phosphohistidine-containing polypeptide.

In a still further aspect of the invention there is provide the use of an analogue according to any one of the phosphohistidine analogues of Formula I, II, III, IV, V and VI to generate an antibody that specifically binds to phosphohistidine.

In another aspect of the present invention there is provided a phosphotyrosine analogue of Formula VII:

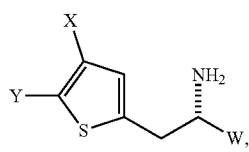

Formula VII wherein
W is selected from H or $CO_2H$;
X is selected from $P(O)(OH)_2$ or H; and
Y is selected from $P(O)(OH)_2$ or H;
with the proviso that when X is selected from $P(O)(OH)_2$, Y is selected from H and when Y is selected from $P(O)(OH)_2$, X is selected from H.

Preferably, W is selected from $CO_2H$.
Preferably, the phosphotyrosine analogue of Formula VII is selected from the group consisting of:

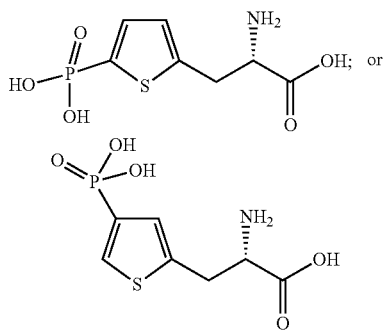

In a further aspect, there is provided a polypeptide comprising the phosphotyrosine analogue of Formula VII.

In yet a further aspect there is provided an antibody or fragment thereof, that binds to an amino acid analogue of the phosphotyrosine analogue of Formula VII.

In one preferred embodiment said antibody that binds to an amino acid analogue of the phosphotyrosine analogue of Formula VII is a polyclonal antibody.

In another preferred embodiment said antibody that binds to an amino acid analogue of the phosphotyrosine analogue of Formula VII is a monoclonal antibody.

In a further aspect said antibody that binds to an amino acid analogue of the phosphotyrosine analogue of Formula VII specifically binds to a phosphotyrosine amino acid residue or analogue thereof.

Preferably, said phosphotyrosine amino acid residue is a residue in a polypeptide.

In a further aspect of the present invention there is provided a method of producing an anti-phosphotyrosine antibody, comprising:
(a) immunizing a non-human animal with an analogue according to the phosphotyrosine analogue of Formula VII;
(b) collecting serum from the immunized animal;
(c) isolating from the serum a population of polyclonal antibodies that bind to the analogue.

In one preferred embodiment of said method of producing an anti-phosphotyrosine antibody, said analogue is provided as a residue in a polypeptide.

In another preferred embodiment of said method of producing an anti-phosphotyrosine antibody, said analogue is coupled to a carrier protein.

Preferably, said carrier protein is selected from keyhole limpet hemocyanin (KLH), or bovine serum albumin (BSA).

In a further preferred embodiment of said method of producing an anti-phosphotyrosine antibody, the binding of said polyclonal antibodies to said analogue is independent of the amino acid sequence of the polypeptide or carrier protein.

In yet a further preferred embodiment of said method of producing an anti-phosphotyrosine antibody, said method further comprises a step of enriching the population of polyclonal antibodies that bind to the analogue.

In a further aspect of the present invention there is provided a polyclonal antibody or fragment thereof or a population of polyclonal antibodies obtainable by said method of producing an anti-phosphotyrosine antibody.

In yet a further aspect of the present invention there is provided a further method of producing an anti-phosphotyrosine antibody, comprising:
(a) immunizing a non-human animal with an analogue according to the phosphotyrosine analogue of Formula VII;
(b) generating hybridomas by fusing B-cells isolated from the immunized animal with myeloma cells;
(c) identifying hybridomas that produce monoclonal antibodies that bind to the analogue; and
(d) propagating said identified hybridomas to produce monoclonal antibodies that bind to the analogue.

In one preferred embodiment of said further method of producing an anti-phosphotyrosine antibody, said analogue is provided as a residue in a polypeptide.

In another preferred embodiment of said further method of producing an anti-phosphotyrosine antibody, said analogue is coupled to a carrier protein.

Preferably, said carrier protein is selected from keyhole limpet hemocyanin (KLH), or bovine serum albumin (BSA).

In a further preferred embodiment of said further method of producing an anti-phosphotyrosine antibody, the binding of said monoclonal antibodies to said analogue is independent of the amino acid sequence of the polypeptide or carrier protein.

In a further aspect of the present invention there is provided a monoclonal antibody or fragment thereof obtainable by said further method of producing an anti-phosphotyrosine antibody.

In a still further aspect of the present invention there is provided a method of detecting a phosphotyrosine-containing polypeptide comprising:
(a) containing a test polypeptide with an antibody or fragment thereof, that binds to the phosphotyrosine analogue of Formula VII or an anti-phosphotyrosine antibody as herein described above; and
(b) detecting binding of said antibody to said test polypeptide,
wherein binding of the antibody to the test polypeptide identifies the polypeptide as containing a phosphotyrosine residue.

In yet a still further aspect of the present invention there is provided the use of an antibody or fragment thereof as herein described above to identify a phosphotyrosine residue or a phosphotyrosine-containing polypeptide.

In a further aspect of the invention there is provided the use of an analogue according to the phosphotyrosine analogue of Formula VII to generate an antibody that specifically binds to phosphotyrosine.

In yet a further aspect of the invention there is provided the use of an analogue according to the phosphotyrosine analogue of Formula VII to inhibit cystic fibrosis transmembrane conductance regulator (CFTR) channel activity.

BRIEF DESCRIPTION OF THE DRAWINGS

Embodiments of the invention are further described herein after with reference to the accompanying drawings, in which:

FIG. 10 shows a general 96 well plate for the competition ELISA using the purified polyclonal antibodies. Each cell shows the concentration of free amino acid in mM.

DETAILED DESCRIPTION

Figure 1:
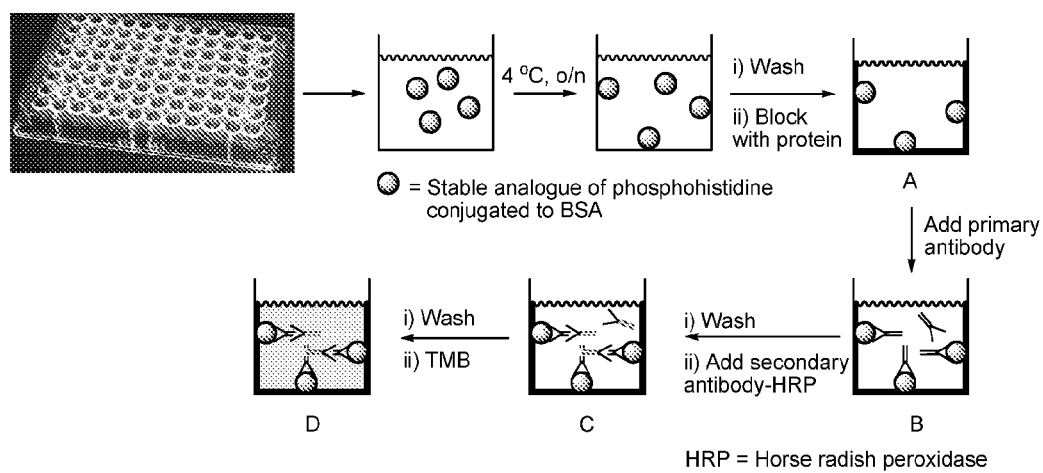
FIG. 1 shows a general ELISA scheme.
Figure 1:
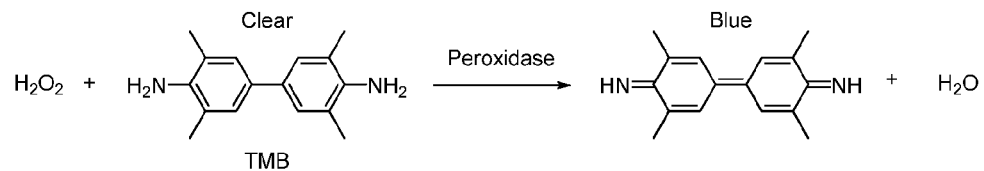

The inventors have identified phosphohistidine analogues which can be used for the production of anti-phosphohistidine antibodies. The inventors have also identified phosphotyrosine analogues which can be used for the production of anti-phosphotyrosine antibodies. Advantageously, antibodies raised against the analogues of the invention specifically recognize phosphohistidine or phosphotyrosine, but not other phosphorylated amino acid residues or unphosphorylated histidine or tyrosine. Most advantageously, the antibodies of the present invention specifically bind phosphohistidine or phosphotyrosine independent of the polypeptide sequence within which the phosphorylated residue occurs.

The antibodies of the invention are useful in biological/medical research for isolating and identifying phosphohistidine and/or phosphotyrosine-containing proteins.

The present invention also provides methods for generating antibodies which specifically react to a polypeptide phosphorylated at a particular amino acid. Methods for generating both monoclonal and polyclonal antibodies are provided. The methods involve providing a polypeptide which has an incorporated analogue of the phosphorylated amino acid residue.

Without being bound by the theory, the inventors have identified the spatial importance of the phosphonate group on the analogue as key to antibody specificity.

Structures of the Analogues

Two isomeric forms phosphohistidine are known (compounds 1, tele-phosphohistidine & 2, pros-phosphohistidine, below):

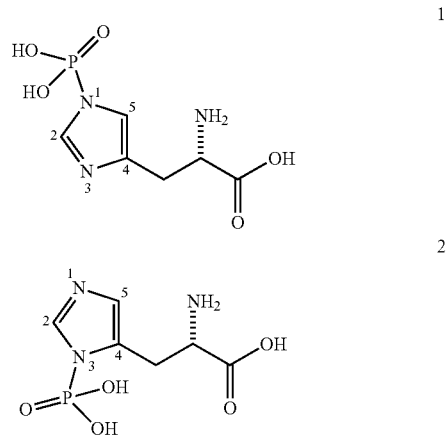

In contrast to the more commonly reported phosphohydroxyamino acids (phosphoserine, phosphothreonine and phosphotyrosine), the phosphoryl group in phosphohistidine is attached to the imidazole ring, as a phosphoramidate bond. This phosphoramidate bond is key to the phosphohistidine's biological function, however it is also acid labile making it difficult to study.

The inventors have surprisingly identified that the spatial location of the phosphoramidate in comparison to the lone pair available on nitrogen in the histidine heterocycle and the functionalized alkyl substituent at C-4 of phosphohistidine is critical to the synthesis of stable analogues of phosphohistidine. The inventors have therefore considered this principle when designing stable structural mimics of phosphohistidine and phosphotyrosine.

As used herein, the term "phosphohistidine analogue" refers to a phosphorylated chemical moiety that is functionally capable of replacing phosphohistidine in a phosphohistidine containing ligand.

Accordingly, in some embodiments the invention provides nitrogen containing heterocyclic systems as analogues of phosphohistidine. In certain embodiments, the nitrogen containing phosphohistidine analogues may comprise a six-membered ring. In some embodiments, the nitrogen containing phosphohistidine analogues can comprise a six membered ring with a 1,4 relationship between a phosphonic acid moiety and a functionalized alkyl substituent, having the general structure of Formula I:

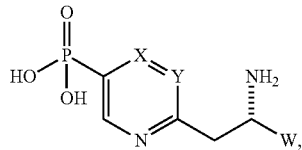

Formula I wherein

X is selected from CH or N;

Y is selected from CH or N; and

W is selected from H, CO$_2$H or CONH$_2$.

In some embodiments of the analogue of Formula I, W is selected from H or CO$_2$H. In some embodiments of the analogue of Formula I, W is selected from CO$_2$H. In other embodiments, W is selected from H. In other embodiments, W is selected from CONH$_2$.

In some embodiments of the analogue of Formula I, X is selected from CH. In other embodiments, X is selected from N.

In some embodiments of the analogue of Formula I, Y is selected from CH. In other embodiments, Y is selected from N.

In some preferred embodiments, the analogue of Formula I is selected from the group consisting of:

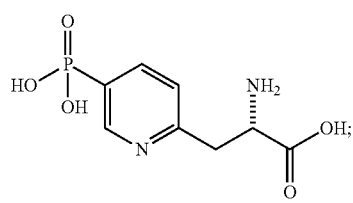 [SMILES: N[C@@H](Cc1ccc(P(=O)(O)O)cn1)C(=O)O]

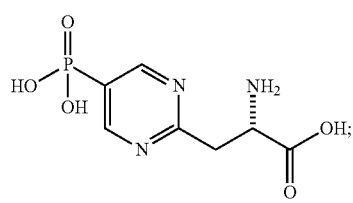

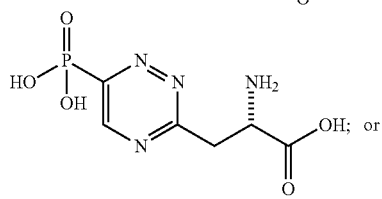
or

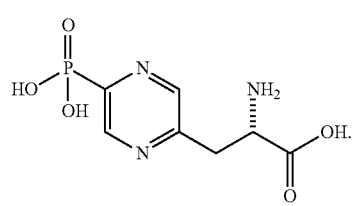

In one preferred embodiment, the analogue of Formula I is:

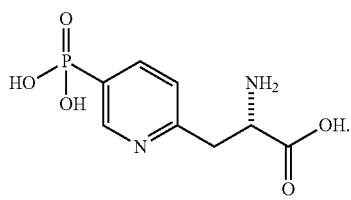

Alternatively, in some embodiments, the nitrogen containing phosphohistidine analogues can comprise a six-membered ring with a 1, 3 relationship between the phosphonic acid moiety and the functionalized alkyl substituent, having the general structure of Formula II:

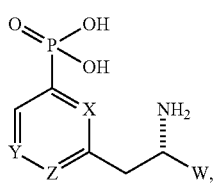

Formula II wherein

X is selected from CH or N;

Y is selected from CH or N;

W is selected from H, CO$_2$H or CONH$_2$; and

Z is selected from CH or N;

with the proviso that at least one of X, Y or Z is selected from N.

In some embodiments of the analogue of Formula II, W is selected from H or CO$_2$H. In some embodiments of the analogue of Formula II, W is selected from CO$_2$H. In other embodiments, W is selected from H. In other embodiments, W is selected from CONH$_2$.

In some embodiments of the analogue of Formula II, X is selected from CH. In other embodiments, X is selected from N.

In some embodiments of the analogue of Formula II, Y is selected from CH. In other embodiments, Y is selected from N.

In some embodiments of the analogue of Formula II, Z is selected from CH. In other embodiments, Z is selected from N.

In some preferred embodiments, the analogue of Formula II is selected from the group consisting of:

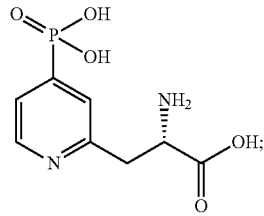

-continued

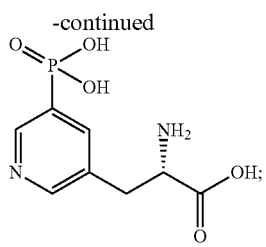

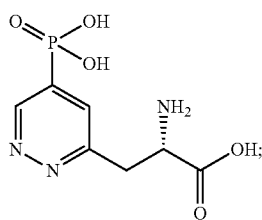

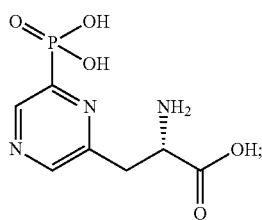

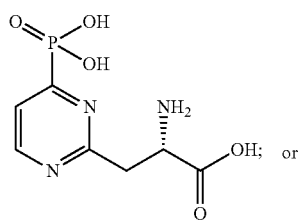 or

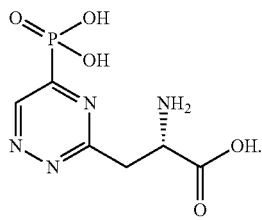

In one preferred embodiment, the analogue of Formula II is:

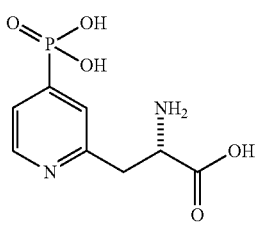 [SMILES: N[C@@H](Cc1cc(P(=O)(O)O)ccn1)C(=O)O]

In further embodiments, the invention provides a system comprising a five-membered nitrogen containing heterocycle as an analogue of phosphohistidine.

In some preferred embodiments of the invention, the phosphohistidine analogue has the general structure of Formula III:

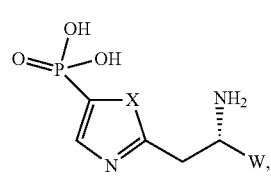

wherein
W is selected from H, $CO_2H$ or $CONH_2$; and
X is selected from NH, O or S.

In some preferred embodiments of Formula III, W is selected from H or $CO_2H$. In some preferred embodiments of Formula III, W is selected from $CO_2H$. In other embodiments, W is selected from H. In other embodiments, W is selected from $CONH_2$.

In some preferred embodiments of Formula III, X is selected from NH. In further embodiments, X is selected from O. In still further embodiments, X is selected from S.

In some preferred embodiments, the analogue of Formula III is selected from the group consisting of:

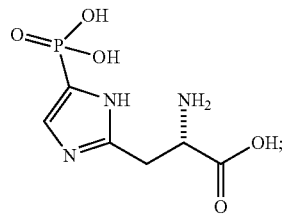

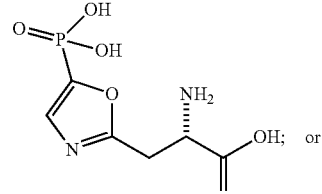 or

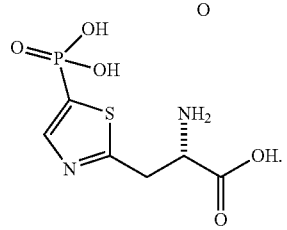

In further preferred embodiments of the invention, the phosphohistidine analogue has the general structure of Formula IV:

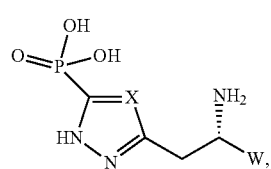

wherein
W is selected from H, $CO_2H$ or $CONH_2$; and
X is selected from CH or N.

In some preferred embodiments of Formula IV, W is selected from H or CO₂H. In some preferred embodiments of Formula IV, W is selected from CO₂H. In other embodiments, W is selected from H. In other embodiments, W is selected from CONH₂.

In some preferred embodiments of Formula IV, X is selected from CH. In other embodiments, X is selected from N.

In one preferred embodiment, the analogue of Formula IV is:

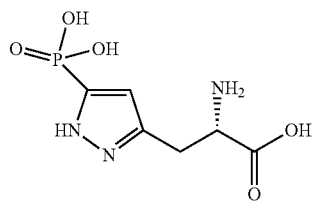 [SMILES: N[C@@H](Cc1cc(P(=O)(O)O)[nH]n1)C(=O)O]

In other preferred embodiments of the invention, the phosphohistidine analogue has the general structure of formula V:

Formula V

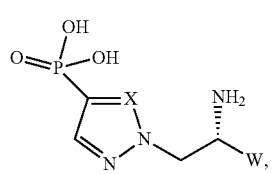

wherein
W is selected from H, CO₂H or CONH₂; and
X is selected from CH or N.

In some preferred embodiments of Formula V, W is selected from H or CO₂H. In some preferred embodiments of Formula V, W is selected from CO₂H. In other embodiments, W is selected from H. In other embodiments, W is selected from CONH₂.

In some preferred embodiments of Formula V, X is selected from CH. In other embodiments, X is selected from N.

In one preferred embodiment, the analogue of Formula V is:

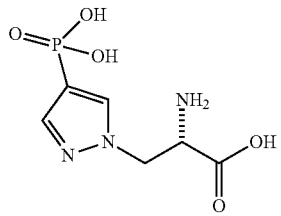 [SMILES: N[C@@H](Cn1cc(P(=O)(O)O)cn1)C(=O)O]

The above-described phosphohistidine analogues comprising six-membered and five-membered nitrogen containing heterocyclic rings provide stable analogues of tele-phosphohistidine. Without wishing to be bound by any particular theory, it is believed that the improved stability is derived from the replacement of the labile phosphoramidate by a stable phosphonic acid, and the successful mimicry of tele-phosphohistidine is derived from the location of the lone pair in said five-membered and said six-membered hetereocyclic rings and its relationship to the functionalized alkyl side chain connected to the heterocycle in comparison to the phosphonic acid moiety.

In some preferred embodiments, the phosphohistidine analogues of the invention abide by a design concept devised to mimic tele-phosphohistidine and maximize their efficacy. Examples of structures that are aligned with this concept include the feature of a nitrogen atom having a basic lone pair that is separated from a carbon bearing a phosphonic acid moiety by an unsaturated CH group. Analogues having such features exhibit the key structural elements of tele-phosphohistidine, but with a stable carbon-phosphorus bond in place of the labile nitrogen-phosphorus bond present in tele-phosphohistidine. Structures that are unified by this concept are distinct from certain triazole-based phosphohistidine analogues disclosed in the prior art that instead include a nitrogen atom in place of the unsaturated CH group as described above.

Thus, in some preferred embodiments, there is provided phosphohistidine analogues that conform to the above-mentioned design concept within the scope of general Formula I, III and V. Particularly, said analogues that conform to the above-mentioned design concept can be selected from the group consisting of:

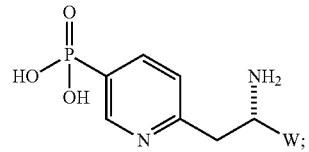

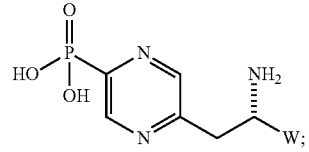

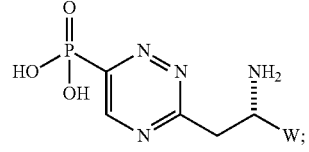

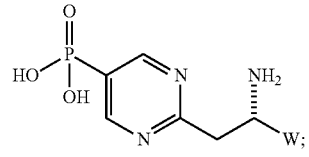

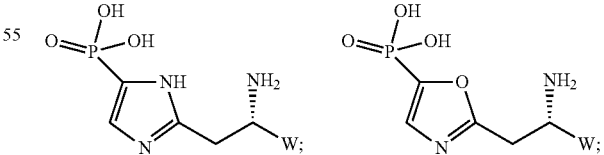

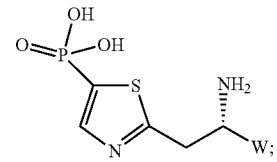

-continued

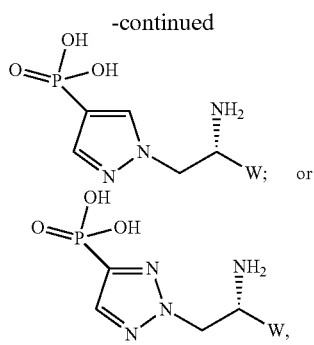

wherein
W is selected from H, $CO_2H$ or $CONH_2$.

In some preferred embodiments of said analogues, W is selected from H or $CO_2H$. In some preferred embodiments of said analogues, W is selected from $CO_2H$. In other embodiments, W is selected from H. In other embodiments, W is selected from $CONH_2$.

In further embodiments, the invention provides a phosphohistidine of the general structure according to Formula VI:

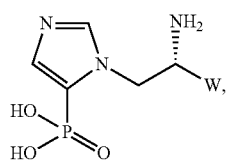

Formula VI wherein
W is selected from H, $CO_2H$ or $CONH_2$.

In some preferred embodiments of Formula VI, W is selected from H or $CO_2H$. In other embodiments, W is selected from $CONH_2$.

The above-described analogues of Formula VI have surprisingly been found to provide stable analogues of pros-phosphohistidine.

As used herein, the term "phosphotyrosine analogue" refers to a phosphorylated chemical moiety that is functionally capable of replacing phosphotyrosine in a phosphotyrosine containing ligand.

In further embodiments, the invention provides phosphotyrosine analogues of Formula VII:

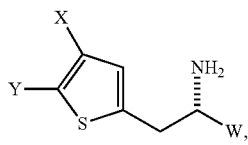

Formula VII wherein
W is selected from H or $CO_2H$;
X is selected from $P(O)(OH)_2$ or H; and
Y is selected from $P(O)(OH)_2$ or H;
with the proviso that when X is selected from $P(O)(OH)_2$, Y is selected from H and when Y is selected from $P(O)(OH)_2$, X is selected from H.

In some preferred embodiments of Formula VII, W is selected from $CO_2H$. In other embodiments, W is selected from H.

In some preferred embodiments of Formula VII, X is selected from $P(O)(OH)_2$ and Y is selected from H. In other embodiments, X is selected from H and Y is selected from $P(O)(OH)_2$.

In some preferred embodiments, the analogue of Formula VII is selected from the group consisting of:

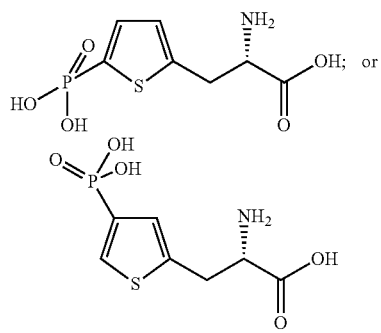

The above-described analogues of Formula VII have surprisingly been found to provide stable analogues of phosphotyrosine.

The analogues of the invention may be incorporated into polypeptide sequences. Methods for this incorporation are known or otherwise available to one of skill in the art. The polypeptide can be produced by chemical synthesis by one of skill in the art through the application of routine experimentation.

As used herein the terms "polypeptide" and "peptide" are used interchangeably to refer to a polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence including the phospho-peptide analogues of the invention.

The analogues of the invention and/or the analogue containing polypeptide of the invention may be further modified to more closely resemble the natural product or, alternatively, to promote antigenicity. The analogues of the invention and/or the analogue containing polypeptide of the invention may thus be subject to one or more modifications including, but not limited to, enzymatic modifications, chemical protection or deprotection, denaturation and chemical coupling.

In a preferred embodiment, the analogue may be coupled to a carrier protein. Such coupling may advantageously promote the antigenicity of the analogue.

Preferably the carrier protein is selected from keyhole limpet hemocyanin (KLH), bovine serum albumin (BSA) or ovalbumin. Coupling of the analogue to a carrier protein may be achieved using methods known in the art, see Coligan J E, Kruisbeek A M, Margulies D H, Shevach E M, Strober W. Current Protocols in Immunology. Vol. 2. New York: John Wiley & Sons; 1996. pp. 9.0.1-9.8.15; and Harlow D L. Antibodies: A Laboratory Manual. New York: Cold Spring Harbor Laboratory; 1988. pp. 72-87. In one embodiment analogues may be couple to carrier proteins via a chemical linker, such as glutaraldehyde, and other amine-reactive crosslinker groups such as NHS-ester crosslinkers including BS(PEG)n or Imidoesters.

Phospho-Specific Antibodies

The present invention provides antibodies that specifically bind to phosphohistidine or phosphotyrosine amino acid residues and to epitopes comprising said phosphorylated residues. Antibodies that specifically bind to phosphohistidine or phosphotyrosine are also referred to as anti-phosphohistidine or anti-phosphotyrosine antibodies, respectively.

Figure 3:
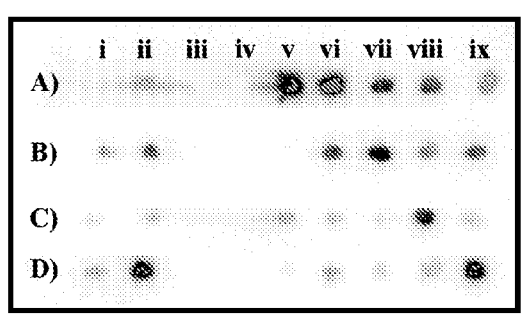
FIG. 3 shows Dot-blots that showed the polyclonal anti-sera selectivity generated from A) 4-phosphothiophen-2-yl alanine, B) 4-phosphopyrid-2-yl alanine, C) 5-phospho-pyrid-2-yl alanine, D) 4-phosphopyrazol-1-yl alanine.
Figure 3:
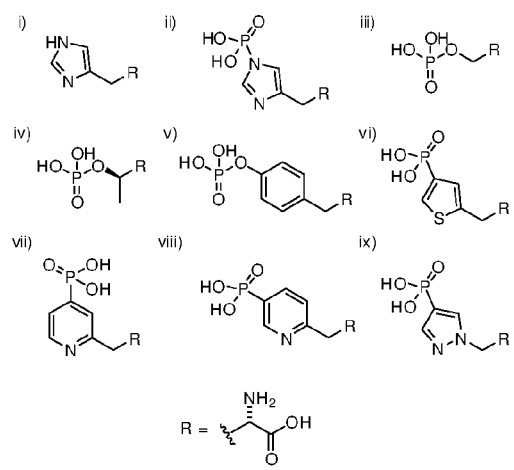

The inventors have demonstrated that polyclonal antibodies raised against 4-phosphopyrid-2-yl alanine detected tele-phosphohistidine strongly in comparison to the other phosphoamino acids (FIG. 3, B).

The polyclonal antibodies raised against 5-phosphopyrid-2-yl alanine also detected tele-phosphohistidine but a similar response to phosphotyrosine also occurred (FIG. 3, C). When the structure of the analogue 5-phosphopyrid-2-yl alanine is compared to the structure of tele-phosphohistidine and phosphotyrosine, it is noted that location of the phosphonate group is similar spatially to the amino acid side chain for both phosphoamino acids.

The polyclonal antibodies raised against 4-phosphopyrazol-1-yl alanine showed the most promising result having the strongest response to tele-phosphohistidine, with a relatively weak detection of histidine (FIG. 3, D). The small amount of cross reactivity for histidine was shown to be due to the glutaraldehyde linker that was used in both the antigen and the test substrate, and could be removed by affinity purification.

The polyclonal antibodies raised against 4-phosphothiophen-2-yl alanine showed a strong response even at a 1000 fold dilution, however the antisera did not appear to detect tele-phosphohistidine or a histidine residue (FIG. 3, A).

In addition, the selectivity for phosphotyrosine that is observed from the polyclonal antibodies generated from 4-phosphothiophen-2-yl alanine can be explained if the nature of the sulfur's lone pair is considered. The lone pair that is present on a thiophene is a poor mimic of the corresponding lone pair on nitrogen present in tele-phosphohistidine. This mismatch of electronics, together with the longer carbon-sulfur bonds, means that the thiophene ring is evidently a better match to a benzene ring, and therefore has led to a polyclonal serum that detects phosphotyrosine over tele-phosphohistidine.

The polyclonal antibodies generated from 4-phosphopyrazol-1-yl alanine, were shown to detect phosphohistidine as part of a dot-blot and as an amino acid conjugated to BSA, more selectively in comparison to polyclonal antibodies from 4-phosphopyrid-2-yl alanine, and 5-phosphopyrid-2-yl alanine.

The polyclonal antisera generated from 4-phosphonothiophen-2-yl alanine had a strong preference for phosphotyrosine over the other remaining phosphohydroxy amino acids and phosphohistidine, a small amount of cross reactivity for phosphohistidine was still observed, but this was shown to be due to the glutaraldehyde linker that was used in both the antigen and the test substrate, and could be removed by affinity purification.

The polyclonal antibodies raised against 4-phosphopyrid-2-yl alanine detected tele-phosphohistidine strongly in comparison to the other phosphoamino acids (FIG. 3, B). The polyclonal antibodies raised against 5-phosphopyrid-2-yl alanine also detected tele-phosphohistidine but a similar response to phosphotyrosine also occurred (FIG. 3, C). Finally the polyclonal antibodies raised against 4-phosphopyrazol-1-yl alanine showed the most promising result having the strongest response to tele-phosphohistidine, with a relatively weak detection of histidine (FIG. 3, D)

Figure 4:
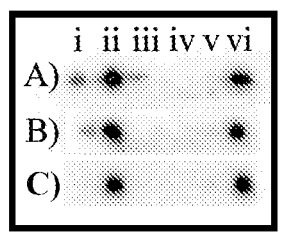
FIG. 4 shows Dot-blots of 4-phosphopyrazol-1-yl alanine generated anti-sera including A) Crude polyclonal antisera, B) Affinity depleted sera using histidine, C) Affinity depleted sera using glutaraldehyde conjugated histidine-KLH; i) Histidine; ii) tele-Phosphohistidine; iii) Phosphoserine; iv) Phosphothreonine; v) Phosphotyrosine; vi) 4-phosphopyrazol-1-yl alanine.
Figure 4:
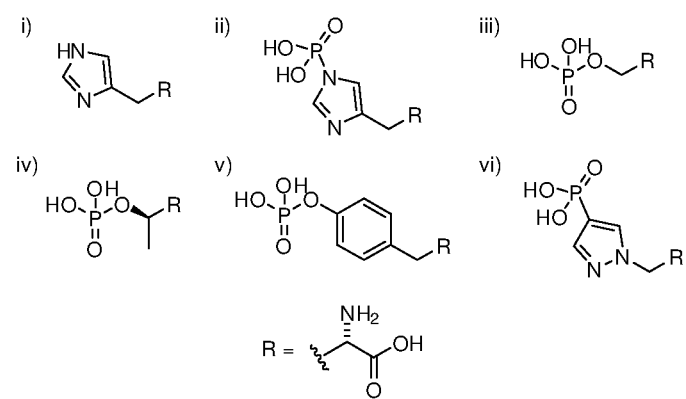

Although the antisera raised from 4-phosphopyrazol-1-yl alanine resulted in the most selective polyclonal antibodies, it appeared to cross-react with histidine. The sample of polyclonal serum was therefore first affinity depleted using histidine bound to a sepharose column but this did not remove the histidine cross-reactivity (FIG. 4, Entry B). The polyclonal antibody was therefore further affinity depleted using glutaraldehyde-conjugated histidine-KLH coupled to a sepharose matrix to give a polyclonal antibody selective for tele-phosphohistidine, with no cross-reactivity to phosphoserine, phosphothreonine or phosphotyrosine (FIG. 4, Entry C).

As used herein, the terms "specifically recognize", "specifically bind" and "specifically immunoreactive" are used interchangeably to refer to binding between an antibody and a polypeptide or amino acid residue that is determinative of the presence of the peptide or amino acid residue in the presence of a heterogeneous population of peptides and other biological molecules. Accordingly, under specified conditions, an antibody specifically binds a particular target polypeptide or amino acid residue and does not bind in a significant amount to other peptides or amino acid residues present in a sample. Preferably, an antibody that specifically binds its intended target, i.e. a phosphorylated histidine or tyrosine residue or an analogue thereof, binds to said target with an affinity of about 5-fold greater, preferably 10 fold, 25-fold, 50-fold, and particularly 100-fold or more, greater for a target molecule than its affinity for a non-target molecule.

In some embodiments, specific binding between an antibody and its target is defined by the association rate (Ka) of the antibody target interaction. Preferably specific binding between an antibody and its target has a binding affinity (Ka) of about $10^3$ $M^{-1}$ or $10^4$ $M^{-1}$, in some embodiments about $10^5$ $M^{-1}$ or $10^6$ $M^{-1}$, in other embodiments $10^6$ $M^{-1}$ or $10^7$ $M^{-1}$, preferably about $10^8$ $M^{-1}$ to $10^9$ $M^{-1}$, more preferably, about $10^{10}$ $M^{-1}$ to $10^{11} M^{-1}$ or higher. In some embodiments, specific binding between an antibody and its target is defined by the disassociation rate (Kd) of the antibody target interaction. Preferably specific binding between an IgG antibody and its target has a Kd of about $1\times10^{-7}$ M or less, more preferably $5\times10^{-8}$ M or less, even more preferably $1\times10^{-8}$ M or less, even more preferably $5\times10^{-9}$ M or less and even more preferably $1\times10^{-9}$ M or less for a target antigen. Alternatively, specific binding between an IgM antibody and its target Kd of $10^{-6}$ M or less, more preferably $10^{-7}$ M or less, even more preferably $10^{-8}$ M or less.

The term "specifically binds" is not intended to indicate that an antibody binds exclusively to its intended target.

As used herein, the term "antibody" refers to an immunoglobulin specifically immunoreactive to a given antigen (e.g., a phosphohistidine or phosphotyrosine residue or analogue thereof). The term "antibody" as used herein is intended to include whole antibodies of any isotype (IgG, IgA, IgM, IgE, IgD), and fragments thereof. An "antibody" of the invention also includes an antibody preparation, e.g., a serum (antiserum). Antibodies can be fragmented using conventional techniques and the fragments screened for utility in the same manner as whole antibodies. Antibody fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites.

Antibodies may be labeled with detectable labels by one of skill in the art. The label can be a radioisotope, fluorescent compound, chemiluminescent compound, enzyme, or enzyme co-factor, or any other labels known in the art.

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments of any of the above. The antibodies of the invention can be from any animal origin including birds and mammals. Preferably, the antibodies are of human, murine (e.g., mouse and rat), donkey, sheep, rabbit, goat, guinea pig, camel, horse, or chicken origin.

As used herein, the terms "polyclonal antibody" and "polyclonal antibodies" refer to an antibody from heterogeneous population of antibody molecules derived from the sera of an immunized animals which are capable of binding to or reacting with several different specific antigenic determinants (also referred to herein as "epitopes") on the same or on different antigens. Preferably, polyclonal antibodies of the invention are prepared by immunization of an animal with the analogues of the invention or polypeptide comprising said analogues.

Polyclonal antibodies of the invention can be produced by various procedures well known in the art (see for example, Sambrook et al., *Molecular Cloning: A Laboratory Manual, Second Edition* (Cold Spring Harbor, N.Y., 1989). For the production of polyclonal antibodies in vivo, host animals, preferably non-human animals such as rabbits, rats, mice, sheep, or goats, are immunized with either free or carrier-coupled peptides comprising or couple to the analogues of the invention, for example, by intraperitoneal and/or intradermal injection. Injection material is typically an emulsion containing about 100 [micro]g of peptide or carrier protein. Various adjuvants can also be used to increase the immunological response, depending on the host species. Adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. Several booster injections may be needed, for instance, at intervals of about two weeks, to provide a useful titer of antibody which can be detected, for example, by ELISA assay using free peptide adsorbed to a solid surface. The titer of antibodies in serum from an immunized animal can be increased by selection of antibodies, e.g., by adsorption of the peptide onto a solid support and elution of the selected antibodies according to methods well known in the art.

Because the peptide antigen used contains antigenic determinants common to both the phospho- and unphosphorylated protein, the serum generated by this method may contain a subset of antibodies which specifically bind the phosphoprotein, and also a subset of antibodies which bind independent of phosphorylation state. Such unwanted binding activities can be cleared or depleted from the antiserum by conventional techniques (Czernik et al., Methods in Enzymology 201: 264-283 (1991)). When necessary, mono-specific antibodies can be purified from the serum using the antigenic determinant in affinity purification (e.g. by affinity chromatography) or conversely, by depleting the serum of all other antibody activity and in this way the population of phospho-specific antibodies may be enriched.

A variety of assays known to those skilled in the art can be utilized to detect antibodies which specifically bind to phosphopeptides and the analogues thereof of the present invention. Exemplary assays are described in detail in Antibodies. A Laboratory Manual, Harlow and Lane (Eds.), (Cold Spring Harbor Laboratory Press, 1988). Representative examples of such assays include: concurrent immuno-electrophoresis, radio-immunoassays, radio-immunoprecipitations, enzyme-linked immunosorbent assays (ELISA), dot blot assays, inhibition or competition assays, and sandwich assays.

As used herein the term "epitope" refers to a site on an antigen that is bound by an antibody. An epitope is also referred to as a determinant or antigenic determinant. Epitopes can be formed both from contiguous amino acids or noncontiguous amino acids juxtaposed by tertiary folding of a protein. An epitope can also be formed by an analogue according to the present invention. Polyclonal antibodies binding to different epitopes on the same antigen can have varying effects on the activity of the antigen they bind depending on the location of the epitope. An antibody binding to an epitope in an active side of the antigen may block the function of the antigen completely, whereas another polyclonal antibody binding at a different epitope may have no or little effect on the activity of the antigen alone.

As used herein, the terms "monoclonal antibody" or "monoclonal antibodies" refer to a preparation of antibodies of single molecular composition. A monoclonal antibody composition displays a single binding specificity and affinity for a particular epitope of a target antigen with which it immunoreacts. A mixture of monoclonal antibodies is not as such considered a polyclonal antibody. A monoclonal antibody is produced by the daughter cells of a single antibody-producing hybridoma.

Monoclonal antibodies may be obtained by methods known to those skilled in the art. Kohler and Milstein (1975), Nature, 256:495-497; U.S. Pat. No. 4,376,110; Ausubel et al. (1987, 1992), eds., Current Protocols in Molecular Biology, Greene Publishing Assoc. and Wiley Interscience, N.Y.; Harlow and Lane (1988), Antibodies: A Laboratory Manual, Cold Spring Harbor Laboratory; Colligan et al. (1992, 1993), eds., Current Protocols in Immunology, Greene Publishing Assoc. and Wiley Interscience, N.Y.; Iyer et al., Ind. J. Med. Res., (2000), 123:561-564. In one embodiment, the monoclonal antibodies are prepared using hybridoma technology, such as those described by Kohler and Milstein (1975), Nature, 256:495. In a hybridoma method, an appropriate host animal, preferably a non-human animal such as a mouse or hamster, is immunized with an immunizing agent (e.g., an analogue of the invention or a polypeptide comprising an analogue of the invention) to elicit lymphocytes that produce or are capable of producing antibodies that will specifically bind to analogue. The lymphocytes are then fused with an immortalized cell line using a suitable fusing agent, such as polyethylene glycol, to form a hybridoma cell. (See Goding, Monoclonal Antibodies: Principles and Practice, Academic Press, (1986) pp. 59-103). Immortalized cell lines are usually transformed mammalian cells such as myeloma cells. The hybridoma cells may be cultured in a suitable culture medium that preferably contains one or more substances that inhibit the growth or survival of the unfused, immortalized cells. The culture medium in which the hybridoma cells are cultured is then assayed for the presence of monoclonal antibodies. Preferably, the binding specificity (i.e., specific binding) of monoclonal antibodies produced by the hybridoma cells is determined by immunoprecipitation or by an in vitro binding assay, which are well known in the art, for example by an enzyme-linked immunoabsorbent assay (ELISA) or by Scatchard analysis (see Munson and Pollard (1980), Anal. Biochem., 107:220). Following identification of antibody producing hybridoma cells, the hybridomas may be subcloned and grown using techniques well known in the art.

After the desired hybridoma cells are identified, the clones may be subcloned by limiting dilution procedures and grown by standard methods. Monoclonal antibodies secreted by the subclones are then isolated and purified from the culture medium or ascites fluid by conventional immunoglobulin purification procedures.

Alternatively, monoclonal antibodies can be made by recombinant DNA methods, such as those described in U.S. Pat. No. 4,816,567. Examples of techniques that can be used to produce antibody fragments such as single-chain Fvs and antibodies include those described in U.S. Pat. Nos. 4,946,778 and 5,258,498; Huston et al. (1991) Methods in Enzymology, 203:46-88; Shu et al. (1993) Proc. Natl. Acad. Sci. USA, 90:7995-7999; and Skerra et al. (1988) Science, 240:1038-1040, each of which is incorporated herein by reference in its entirety.

The antibodies of the present invention may be chimeric antibodies or humanized antibodies. As used herein, "chimeric antibodies" refers to recombinant antibodies in which all of the V-regions of a mouse or rat antibody are combined with human antibody C-regions. Humanized antibodies are recombinant hybrid antibodies which fuse the complementarity determining regions from a rodent antibody V-region with the framework regions from the human antibody V-regions. The C-regions from the human antibody are also used. The complementarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Uses

The antibodies or fragments of the invention may be labeled, preferably radiolabled, and can be used for in vitro assays, such as assays to discriminate between phosphorylated and non-phosphorylated forms of a test compound.

Methods for labeling antibodies and other biological agents with radioactive isotopes are well known in the art. Fluorophore and chromophore labeled antibodies or fragments thereof can be prepared from standard moieties known in the art.

The antibodies of the invention may be used in to identify phosphohistidine residues or phosphotyrosine residues, for example in assays for analysis of protein phosphorylation, i.e. in order to determine the state of phosphorylation of a test protein. Although all assays that perform this function are contemplated by this invention, direct binding assays are less preferred because they tend to be difficult to carry out in a high-throughput manner. Competitive binding assays are preferred because they are more easily and quickly performed with a large number of non-phosphorylated test compounds.

Particularly preferred competitive binding immunoassays useful in the methods of this invention include, but are not limited to, enzyme-linked, fluorescent, chemiluminescent, radio and biosensor immunoassays. Although the immunoassays of this invention may be carried out in solution or on a solid support, a solid support (such as the wells of a microtiter plate) is preferred to facilitate large-scale screening of non-phosphorylated test compounds. Preferably, the immunoassay used in the methods of this invention is ELISA, a fluorescent immunoassay or a biosensor immunoassay.

The antibodies or fragments thereof of the present invention can be used and sold together with equipment, as a kit, to detect the particular label.

In addition, the antibodies, analogues and/or peptides containing the analogues of the present invention can be used as affinity ligands and/or inhibitors for proteins or enzymes that recognize or bind phosphohistidine or phosphotyrosine. Thus in some embodiments, the analogues of general Formula I, II, III, IV, V and VI can be used as affinity ligands and/or inhibitors for proteins or enzymes that recognize or bind phosphohistidine. In other embodiments, the analogues of general Formula VII can be used as affinity ligands and/or inhibitors for proteins or enzymes that recognize or bind phosphotyrosine.

Furthermore, the inventors believe that the phosphotyrosine analogues of Formula VII can be used to inhibit cystic fibrosis transmembrane conductance regulator (CFTR) channel activity.

Examples

1. Synthesis of Analogues 1.1 General Methods 1.1.1 Physical and Spectroscopic Data Optical rotations were measured on an AA-10 Automatic Polarimeter, at 589 nm, using solutions in indicated solvents. All values are reported in the following format: $[\alpha]_D$ (temperature of measurement)=specific rotation (concentration of the solution reported in units of 10 mg sample per 1 mL solvent, solvent used). Proton, carbon, and phosphorus NMR spectra were measured on either a Bruker DPX-400 or AV250 ($^1$H at 400 MHz, $^{13}$C at 101 MHz, $^{31}$P at 101 MHz) magnetic resonance spectrometer. 1H chemical shifts are reported in parts per million (ppm), coupling constants (J) are reported in Hertz (Hz). Proton (1H) NMR information is tabulated in the following format: multiplicity, coupling constant, number of protons. Multiplicities are reported as follows: s=singlet, d=doublet, t=triplet, dd=doublet of doublets m=multiplet. Proton decoupled 13C NMR spectra are reported in ppm (δ) relative to residual CHCl3 (δ 77.0) unless noted otherwise. Infrared spectra were recorded on a Perkin-Elmer RX I FT-IR Spectrometer using neat material on a NaCl plate or diamond tip. All values are reported in wave numbers (cm$^{-1}$) and are externally referenced to polystyrene film (1601 cm$^{-1}$). ESI-MS was performed on a MicroMass LCT mass spectrometer. Melting Points were determined using Linkam HFS91 heating stage, with a TC 94 controller.

1.2. Preparation of Compounds of Formula I: (2S)-2-(carboxyamino)-3-(5-phosphonopyridin-2-yl)propanoic acid

1.2.1 Methyl (2S)-3-(5-bromopyridin-2-yl)-2-{[(tert-butoxy)carbonyl]amino}propanoate, Compound 4

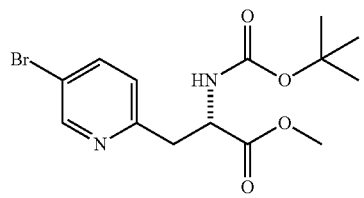 [SMILES: COC(=O)[C@H](Cc1ccc(Br)cn1)NC(=O)OC(C)(C)C]

Zinc dust (1.18 g, 18 mmol, 3 eqv) was added to a flame dried nitrogen purged side arm round bottom flask. DMF (6 mL) was added via syringe followed by a sub-stoichiometric amount of iodine (240 mg, 0.9 mmol). Once the reaction mixture had turned colourless N-(tert-Butoxycarbonyl)-3-iodo-L-alanine methyl ester (1.97 g, 6 mmol, 1 eqv) was added. The reaction mixture was stirred at room temperature and gave a noticeable exotherm. Once the reaction mixture had cooled Pd(PPh$_3$)$_2$Cl$_2$ (211 mg, 0.3 mmol, 0.05 eqv), and 2, 5, dibromopyridine (1.848 g, 7.8 mmol, 1.3 eqv) were added to the flask. The reaction was heated to 50° C. and left stirring overnight, under a positive pressure of nitrogen. The reaction mixture was then partitioned between EtOAc and Brine, followed by extraction of the aqueous layer with EtOAc (2×). The organic layers were then combined, dried with MgSO$_4$, and concentrated under reduced pressure. The crude compound was then purified by silica gel column using 15% EtOAc/85% 40-60 petroleum ether to afford the desired compound 4 (1.38 g, 3.84 mmol, 64% yield).

Thick yellow oil; $\delta_H$ (400 MHz, CDCl$_3$) 1.44 (s, 9H), 3.25 (dd, J=5.5, 15.0 Hz, 1H), 3.31 (dd, J=5.5, 15.0 Hz, 1H), 3.72 (s, 3H), 4.70 (td, J=5.5, 8.5 Hz, 1H), 5.72 (d, J=8.5 Hz, 1H), 7.07 (d, J=8.5 Hz, 1H), 7.75 (dd, J=2.5, 8.5 Hz, 1H), 8.58 (d, J=2.5 Hz, 1H); $\delta_C$ (101 MHz, CDCl$_3$) 28.3, 38.8, 52.3, 52.7, 79.8, 119.0, 125.0, 139.1, 150.0, 155.2, 155.7, 172.0; $[\alpha]_D^{22}$ −12 (c 0.9, Acetone), $[\alpha]_D^{22}$ +29 (c 1.0, CHCl$_3$), lit. value $[\alpha]_D^{17}$ −13.3 (c 0.9, Acetone). Proton and carbon NMR in agreement with the literature (Synthetic Communications 2009, 39, 523).

1.2.2 Methyl (2S)-2-{[(tert-butoxy)carbonyl]amino}-3-[5-(diethoxyphosphoryl)pyridin-2-yl]propanoate, Compound 5

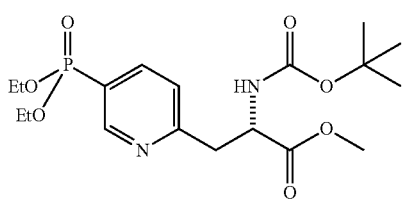 [SMILES: CCOP(=O)(OCC)c1ccc(C[C@H](NC(=O)OC(C)(C)C)C(=O)OC)nc1]

Palladium acetate (13 mg, 0.06 mmol, 0.03 eqv), dppf (67 mg, 0.12 mmol, 0.06 eqv), and sodium acetate (10 mg, 0.24 mmol, 0.12 eqv) were added to a round bottom flask with condenser, before being purged with nitrogen, by applying three cycles of vacuum, followed by nitrogen. Dry THF (4 mL) was then added by syringe followed by $^i$Pr$_2$EtN (310 mg, 0.418 mL, 2.4 mmol, 1.2 eqv). The reaction mixture was then stirred at 60° C. for 30 minutes, before addition of compound 4 (718 mg, 2 mmol, 1 eqv) and diethyl phosphite (278 mg, 0.259 mL, 2 mmol, 1 eqv). The reaction mixture was then brought to reflux and left for 24 hours. The crude reaction mixture was then concentrated by reduced pressure and applied directly to a silica gel column for purification, using 15% MeOH/85% EtOAc, to afford the desired compound 5 (558 mg, 1.34 mmol, 67% yield).

Thick yellow oil; $\nu_{max}$ (film)/cm$^{-1}$ 3284, 2980, 2931, 1748, 1714, 1591, 1553, 1520, 1438, 1392, 1367, 1288, 1252, 1167, 1097, 1052, 1022; $\delta_H$ (400 MHz, CDCl$_3$) 1.36 (t, J=7.0 Hz, 6H), 1.44 (s, 9H), 3.28-3.49 (m, 2H), 3.72 (s, 3H), 4.04-4.29 (m, 4H), 4.69-4.81 (m, 1H), 5.75 (d, J=8.5 Hz, 1H), 7.21-7.30 (m, 1H), 8.02 (ddd, J=2.0, 8.0, 13.0 Hz, 1H), 8.87 (dd, J=2.0, 6.5 Hz, 1H); $\delta_C$ (101 MHz, CDCl3) 16.3 (d, J=6.5 Hz), 28.2 (s), 39.5 (s), 52.3 (s), 62.5 (d, J=6.0 Hz), 79.8 (s), 122.8 (d, J=191.0 Hz), 123.4 (d, J=12.0 Hz), 139.8 (d, J=8.5 Hz), 151.7 (d, J=12.5 Hz), 155.4 (s), 161.3 (s), 172.1 (s); $\delta_P$ (101 MHz, CDCl$_3$) 16.05; $[\alpha]_D^{22}$ +28 (c 1.0, CHCl$_3$); m/z (ES) Found: MH+ 417.1788 C$_{18}$H$_{30}$N$_2$O$_7$P requires MH+ 417.1791.

1.2.3 (2S)-2-(carboxyamino)-3-(5-phosphonopyridin-2-yl)propanoic acid, Compound 6 (Also Referred to Herein as 5-phosphopyrid-2-ylalanine)

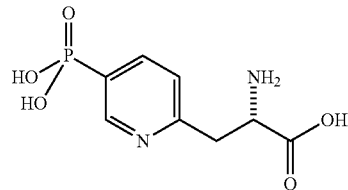 [SMILES: N[C@@H](Cc1ccc(P(=O)(O)O)cn1)C(=O)O]

Compound 5 (208 mg, 0.5 mmol) was added to a round bottom flask with a condenser containing 6M HCl (5 mL), the reaction mixture was then brought to reflux and left overnight. The solvent was then removed from the reaction mixture via reduced pressure and the resulting residue was triturated using isopropanol to give the desired compound 6 (41 mg, 0.17 mmol, 34% yield).

Amorphous cream solid; m.p. 270° C. (decamp.); $\nu_{max}$ (film)/cm$^{-1}$ 2850, 2659, 2341, 1674, 1635, 1615, 1575, 1525, 1425, 1395, 1365, 1332, 1235, 1193, 1136, 1077, 1055; $\delta_H$ (400 MHz, D$_2$O) 3.28 (br s, 2H), 4.14 (br s, 1H), 7.68 (br s, 1H), 8.29 (br s, 1H), 8.48 (br s, 1H); $\delta_C$ (101 MHz, D$_2$O) 34.7 (s), 53.0 (s), 127.2 (d, J=11.0 Hz), 134.0 (d, J=174.5 Hz), 144.2 (d, J=16.5 Hz), 146.5 (s), 153.7 (s), 171.8 (5); $\delta_P$ (101 MHz, D$_2$O) 7.85; $[\alpha]_D^{22}$ +40 (c 1.0, H$_2$O); m/z (ES) Found: MH+ 247.0477 C$_8$H$_{12}$N$_2$O$_5$P requires MH$^+$ 247.0484.

1.3. Preparation of Compounds of Formula II: (2S)-2-Amino-3-(4-phosphonopyridin-2-yl)propanoic acid, Compound 3

1.3.1 Diethyl (2-chloropyridin-4-yl)phosphonate, Compound 1

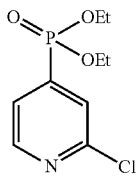

Palladium acetate (34 mg, 0.15 mmol, 0.03 eqv), dppf (166 mg, 0.3 mmol, 0.06 eqv), and sodium acetate (49 mg, 0.6 mmol, 0.12 eqv) were added to a round bottom flask with condenser, before being purged with nitrogen, by applying three cycles of vacuum, followed by nitrogen. Dry THF (10 mL) was then added by syringe followed by $^{i}Pr_2EtN$ (0.775 g, 1.05 mL, 6 mmol, 1.2 eqv). The reaction mixture was then stirred at 60° C. for 30 minutes, before addition of 2-chloro-4-iodopyridine (1.197 g, 5 mmol, 1 eqv) and diethyl phosphate (0.691 g, 0.644 mL, 5 mmol, 1 eqv). The reaction mixture was then brought to reflux and left for 24 hours. The crude reaction mixture was then concentrated by reduced pressure and applied directly to a silica gel column for purification, using EtOAc, to afford the desired compound 1 (616 mg, 2.45 mmol, 49% yield).

Pale yellow oil; $v_{max}$ (film)/cm$^{-1}$ 3483, 3292, 3062, 2984, 2931, 2900, 1749, 1715, 1582, 1531, 1476, 1455, 1393, 1359, 1260, 1164, 1112, 1091, 1050, 1020; $\delta_H$ (400 MHz, CDCl$_3$) 1.37 (td, J=0.5, 3.5 Hz, 6H), 4.11-4.26 (m, 4H), 7.59 (ddd, J=1.0, 5.0, 12.5 Hz, 1H), 7.71 (d, J=13.5 Hz, 1H), 8.54-8.57 (m, 1H); $\delta_C$ (101 MHz, CDCl$_3$) 16.3 (d, J=6.0 Hz), 63.1 (d, J=5.5 Hz), 123.7 (d, J=8.0 Hz), 126.3 (d, J=9.5 Hz), 141.1 (d, J=185.0 Hz), 150.2 (d, J=14.0 Hz), 152.2 (d, J=18.5 Hz); $\delta_P$ (101 MHz, CDCl$_3$) 12.54 (s); m/z (ES) Found: MH$^+$ 250.0406 C$_9$H$_{14}$NO$_3$ClP requires MH$^+$ 250.0400.

1.3.2 Methyl (2S)-2-{[(tert-butoxy)carbonyl]amino}-3-[4-(diethoxyphosphoryl)pyridin-2-yl]propanoate, Compound 2

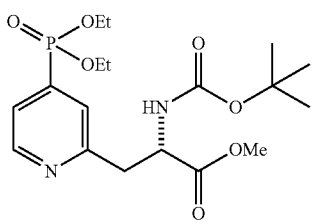 [SMILES: CCOP(=O)(OCC)c1ccnc(C[C@H](NC(=O)OC(C)(C)C)C(=O)OC)c1]

Zinc dust (294 mg, 4.5 mmol, 3 eqv) was added to a flame dried nitrogen purged side arm round bottom flask. DMF (1.5 mL) was added via syringe followed by a sub-stoichiometric amount of iodine (60 mg, 0.225 mmol, 0.15 eqv). Once the reaction mixture had turned colourless N-(tert-Butoxycarbonyl)-3-iodo-L-alanine methyl ester (494 mg, 1.5 mmol, 1 eqv) was added. The reaction mixture was stirred at room temperature and gave a noticeable exotherm. Once the reaction mixture had cooled Pd$_2$(dba)$_3$ (0.025 eqv), SPhos (0.05 eqv), and compound 1 (486 mg, 1.95 mmol, 1.3 eqv) were added to the flask. The reaction was heated to 50° C. and left stirring overnight, under a positive pressure of nitrogen. The reaction mixture was then partitioned between EtOAc and Brine, followed by extraction of the aqueous layer with EtOAc (2×). The organic layers were then combined, dried with MgSO$_4$, and concentrated under reduced pressure. The crude compound was then purified by silica gel column using 80% EtOAc/20% 40-60 petroleum ether to afford the desired compound 2 (262 mg, 0.62 mmol 42% yield).

Thick pale yellow oil; $v_{max}$ (film)/cm$^{-1}$ 3427, 3284, 3054, 2983, 2934, 2908, 1746, 1712, 1594, 1546, 1499, 1438, 1392, 1367, 1265, 1166, 1128, 1097, 1052, 1023; $\delta_H$ (400 MHz, CDCl$_3$) 1.36 (t, J=7.0 Hz, 6H), 1.44 (s, 9H), 3.35 (dd, J=4.5, 15.0 Hz, 1H), 3.43 (dd, J=5.5, 15 Hz, 1H), 3.72 (s, 3H), 4.09-4.26 (m, 4H), 4.70-4.79 (m, 1H), 5.74 (d, J=8.5 Hz, 1H), 7.50-7.57 (m, 2H), 8.68 (t, J=5.5 Hz, 1H); $\delta_C$ (101 MHz, CDCl$_3$) 16.3 (d, J=6.0 Hz), 28.2 (s), 39.4 (s), 52.3 (s), 52.8 (s), 62.9 (d, J=5.5 Hz), 79.9 (s), 123.3 (d, J=8.0 Hz), 125.4 (d, J=8.5 Hz), 138.0 (d, J=186.0 Hz), 149.4 (d, J=13.0 Hz), 155.4 (s), 157.9 (d, J=13.0), 172.1 (s); $\delta_P$ (162 MHz, CDCl$_3$) 14.51; $[\alpha]_D^{22}$ +30 (c 1.0, CHCl$_3$); m/z (ES) Found: MH$^+$ 417.1783 C$_{18}$H$_{30}$N$_2$O$_7$P requires MH$^+$ 417.1791.

1.3.3 (2S)-2-Amino-3-(4-phosphonopyridin-2-yl)propanoic acid, Compound 3 (Also Referred to Herein as 4-phosphopyrid-2-yl alanine)

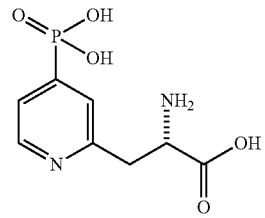 [SMILES: N[C@@H](Cc1cc(P(=O)(O)O)ccn1)C(=O)O]

Compound 2 (208 mg, 0.5 mmol) was added to a round bottom flask with a condenser containing 6M HCl (5 mL), the reaction mixture was then brought to reflux and left overnight. The solvent was then removed from the reaction mixture via reduced pressure and the resulting residue was triturated using isopropanol to give the desired compound 3 (39 mg, 0.16 mmol, 32% yield).

Amorphous cream solid; m.p. 460° C. (decamp.); $v_{max}$ (film)/cm$^{-1}$ 3398, 1598, 1481, 1426, 1094, 1014; $\delta_H$ (400 MHz, D$_2$O) 2.77 (dd, J=9.0, 13.5 Hz, 1H), 3.08 (dd, J=5.0, 13.5 Hz, 1H), 3.51 (dd, J=5.0, 9.0 Hz, 1H), 7.37-7.46 (m, 2H), 8.28-8.32 (m, 1H); $\delta_C$ (101 MHz, D$_2$O) 42.7 (s), 56.8 (s), 123.3 (d, J=7.5 Hz), 125.3 (d, J=7.5 Hz), 147.7 (d, J=11.0 Hz), 151.1 (d, J=160.0 Hz), 157.2 (d, J=10.5 Hz), 182.1 (5); $\delta_P$ (101 MHz, D$_2$O) 4.02; $[\alpha]_D^{22}$ +26 (c 1.0, H$_2$O); m/z (ES) Found: MH$^+$ 247.0477 C$_8$H$_{12}$N$_2$O$_5$P requires MH$^+$ 247.0484.

1.4. Preparation of Compounds of Formula V: (2S)-2-(carboxyamino)-3-(4-phosphono-1H-pyrazol-1-yl) propanoic acid

1.4.1 (2S)-2-{[(tert-butoxy)carbonyl]amino}-3-(4-iodo-1H-pyrazol-1-yl)propanoic acid, Compound 8

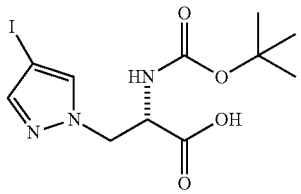 [SMILES: CC(C)(C)OC(=O)N[C@@H](Cn1cc(I)cn1)C(=O)O]

N-Boc-L-serine β-lactone (935 mg, 5 mmol, 1 eqv) in a solution of MeCN (5 mL) was added to a round bottom flask, followed by the addition of 4-iodopyrazole (1.164 g, 6 mmol, 1.2 eqv). The reaction mixture was then heated to 50° C. and left stirring overnight. The reaction was then concentrated by reduced pressure, and partitioned with Et$_2$O, followed by washing the aqueous layer with Et$_2$O (2x). The aqueous layer was then carefully acidified to pH 5, using 1M HCl, before partitioning with EtOAc, followed by a extraction of the aqueous layer with EtOAc (4x) while maintaining the aqueous layer at pH 5. The EtOAc layers were then combined, dried with MgSO$_4$, and the solvent removed via reduced pressure to give the pure compound 8 (991 mg, 2.6 mmol, 52% yield).

Amorphous white solid; m.p. 141-146° C.; $v_{max}$ (film)/cm$^{-1}$ 3336, 3123, 2980, 2922, 2847, 1707, 1513, 1454, 1394, 1368, 1302, 1276, 1251, 1164, 1113, 1063, 1026; $\delta_H$ (400 MHz, CDCl$_3$) 1.49 (s, 9H), 4.51-4.56 (m, 1H), 4.70 (dd, J=4.5, 14.5 Hz, 1H), 4.77 (dd, J=2.0, 14.5 Hz, 1H), 5.50 (d, J=5.5 Hz, 1H), 7.47 (s, 1H), 7.65 (s, 1H), carboxylic acid proton not observed; $\delta_C$ (101 MHz, CDCl$_3$) 28.3 (s), 52.6 (s), 53.9 (s), 56.6 (s), 80.7 (s), 136.0 (s), 145.2 (s), 155.4 (s), 171.0 (s); $[\alpha]_D^{22}$ +71 (c 1.0, CHCl$_3$); m/z (ES) Found: MH$^+$ 382.0265 C$_{11}$H$_{17}$N$_3$O$_4$I requires MH$^+$ 382.0263.

1.4.2 Methyl 2-{[(tert-butoxy)carbonyl]amino}-3-(4-iodo-1H-pyrazol-1-yl)propanoate, Compound 9

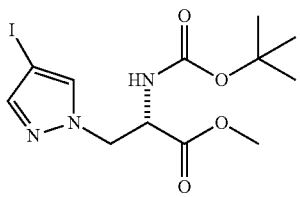 [SMILES: COC(=O)[C@H](Cn1cc(I)cn1)NC(=O)OC(C)(C)C]

Compound 8 (1.143 g, 3 mmol, 1 eqv) in a solution of MeCN was added to a round bottom flask containing K$_2$CO$_3$ (636 mg, 4.6 mmol, 1.2 eqv), the reaction was allowed to stir for 30 minutes, before being cooled to 0° C. and MeI (852 mg, 374 μL, 6 mmol, 2 eqv) slowly added to the reaction. After complete addition of the MeI the reaction was allowed to warm up to room temperature and left overnight stirring. The reaction mixture was then concentrated via reduced pressure and partitioned between 0.1 M NaOH and EtOAc, the aqueous was then extracted with EtOAc (2x). The organic layers were then combined, dried using MgSO$_4$, and the solvent removed using reduced pressure resulting in the desired product (1.067 g, 2.7 mmol, 90% yield).

Thick colourless oil; $v_{max}$ (film)/cm$^{-1}$ 3235, 3118, 3056, 3004, 2978, 2943, 1748, 1696, 1551, 1477, 1450, 1431, 1356, 1298, 1282, 1254, 1220, 1201, 1162, 1026; $\delta_H$ (400 MHz, CDCl$_3$) 1.47 (s, 9H), 3.79 (s, 3H), 4.51-4.68 (m, 3H), 5.64 (d, J=5.64, 1H), 7.40 (s, 1H), 7.52 (s, 1H); $\delta_C$ (101 MHz, CDCl$_3$) 28.3 (s), 30.9 (s), 52.9 (s), 53.0 (s), 53.9 (s), 80.5 (s), 134.9 (s), 145.3 (s), 155.1 (s), 170.0 (s); $[\alpha]_D^{22}$ +35 (c 1.0, CHCl$_3$); m/z (ES) Found: MH$^+$ 396.0416 C$_{12}$H$_{19}$N$_3$O$_4$I requires MH$^+$ 396.0420.

1.4.3 Methyl 2-{[(tert-butoxy)carbonyl]amino}-3-[4-(diethoxyphosphoryl)-1H-pyrazol-1-yl]propanoate, Compound 10

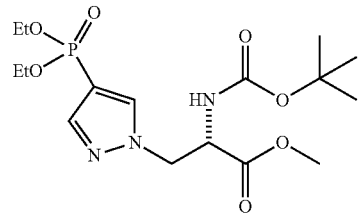 [SMILES: CCOP(=O)(OCC)c1cnn(C[C@H](NC(=O)OC(C)(C)C)C(=O)OC)c1]

Palladium acetate (16 mg, 0.075 mmol, 0.03 eqv), dppf (83 mg, 0.15 mmol, 0.06 eqv), and sodium acetate (25 mg, 0.3 mmol, 0.12 eqv) were added to a round bottom flask with condenser, before being purged with nitrogen, by applying three cycles of vacuum, followed by nitrogen. Dry THF (5 mL) was then added by syringe followed by $^i$Pr$_2$EtN (388 mg, 523 μL, 3 mmol, 1.2 eqv). The reaction mixture was then stirred at 60° C. for 30 minutes, before addition of compound 9 (988 mg, 2.5 mmol, 1 eqv) and diethyl phosphite (345 mg, 322 μL, 2.5 mmol, 1 eqv). The reaction mixture was then brought to reflux and left for 24 hours. The crude reaction mixture was then concentrated by reduced pressure and applied directly to a silica gel column for purification, using EtOAc, to afford the desired compound 10 (648 mg, 1.6 mmol, 64% yield).

Amorphous yellow solid; m.p. 103-106° C.; $v_{max}$ (film)/cm$^{-1}$ 3273, 2978, 2944, 1725, 1531, 1440, 1390, 1366, 1339, 1301, 1271, 1255, 1224, 1163, 1137, 1103, 1051, 1019, 1000; $\delta_H$ (400 MHz, CDCl$_3$) 1.34 (dt, J=1.5, 7.0 Hz, 6H), 1.46 (s, 9H), 3.79 (s, 3H), 4.01-4.18 (m, 4H), 4.58 (dd, J=5.5 Hz, 15.0 Hz, 1H), 4.63-4.73 (m, 2H), 5.44 (d, J=7.0 Hz, 1H), 7.72 (d, J=2.0 Hz, 1H), 7.74 (s, 1H); $\delta_C$ (101 MHz, CDCl$_3$) 16.2 (d, J=6.5 Hz), 28.2 (s), 52.75 (s), 52.8 (s), 53.7 (s), 61.9 (d, J=5.5 Hz), 80.3 (s), 108.0 (d, J=221.0), 136.0 (d, J=23.5 Hz), 143.0 (d, J=13.0 Hz), 155.1 (s), 169.9 (s); $\delta_P$ (101 MHz, CDCl$_3$) 13.25; $[\alpha]_D^{22}$ +29 (c 1.0, CHCl$_3$); m/z (ES) Found: MH$^+$ 406.1745 C$_{16}$H$_{29}$N$_3$O$_7$P requires MH$^+$ 406.1743.

1.4.4 (2S)-2-{[(tert-butoxy)carbonyl]amino}-3-[4-(diethoxyphosphoryl)-1H-pyrazol-1-yl]propanoic acid, Compound 11

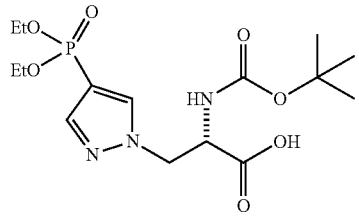 [SMILES: CCOP(=O)(OCC)c1cnn(C[C@H](NC(=O)OC(C)(C)C)C(=O)O)c1]

Compound 10 (203 mg, 0.5 mmol, 1 eqv) was added to a round bottom flask followed by the H$_2$O (1 mL) and THF (1 mL). Once dissolved LiOH (14 mg, 0.6 mmol, 1.2 eqv) was added and the reaction was monitored via TLC until the starting material spot had disappeared. The reaction was then concentrated by reduced pressure, and partitioned with Et$_2$O, followed by washing the aqueous layer with Et$_2$O (2×). The aqueous layer was then carefully acidified to pH 5, using 1M HCl, before partitioning with EtOAc, followed by a extraction of the aqueous layer with EtOAc (4×) while maintaining the aqueous layer at pH 5. The EtOAc layers were then combined, dried with MgSO$_4$, and the solvent removed via reduced pressure to give the pure compound 11 (196 mg, 0.5 mmol, <99% yield).

Thick yellow oil, $v_{max}$ (film)/cm$^{-1}$ 3346, 3119, 2981, 2932, 2571, 1713, 1531, 1443, 1392, 1367, 1339, 1313, 1227, 1165, 1054, 1024; $\delta_H$ (400 MHz, CDCl$_3$) 1.30-1.35 (m, 6H), 1.47 (s, 9H), 4.05-4.18 (m, 4H), 4.57-4.72 (m, 2H), 4.77 (d, J=13.5 Hz, 1H), 5.63 (d, J=6.5 Hz, 1H), 7.80 (s, 1H), 7.90 (s, 1H), carboxylic acid proton not observed; $\delta_C$ (101 MHz, CDCl$_3$) 16.2 (d, J=7.0 Hz), 28.3 (s), 52.9 (s), 53.8 (s), 62.5 (d, J=5.0 Hz), 80.3 (s), 107.1 (d, J=223.0 Hz), 136.6 (d, J=24.5 Hz), 142.8 (d, J=13.5 Hz), 155.4 (s), 170.8 (5); $\delta_P$ (101 MHz, CDCl$_3$) 13.93; [α]$_D^{22}$ −30 (c 1.0, CHCl$_3$); m/z (ES) Found: MH$^+$ 392.1592 C$_{15}$H$_{27}$N$_3$O$_7$P requires MH$^+$ 392.1587.

1.4.5 (2S)-2-(carboxyamino)-3-(4-phosphono-1H-pyrazol-1-yl)propanoic acid, Compound 12 (Also Referred to Herein as 4-phosphopyrazol-1-yl alanine)

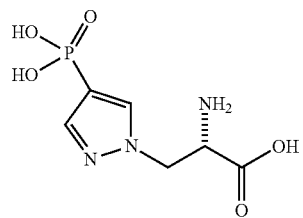 [SMILES: N[C@@H](Cn1cc(P(=O)(O)O)cn1)C(=O)O]

Compound 11 (196 mg, 0.5 mmol, 1 eqv) in a solution of MeCN (5 mL) was added to a round bottom flask, followed by the addition of trimethylsilyl bromide (765 mg, 660 μL, 5 mmol, 10 eqv). The reaction mixture was then brought up to 50° C. and left overnight. The solvent was then removed from the reaction mixture via reduced pressure and the resulting residue was triturated using H$_2$O and isopropanol to give the desired compound 12 (60 mg, 0.26 mmol, 51% yield).

Amorphous cream solid; m.p. 200° C. (decamp.); $v_{max}$ (film)/cm$^{-1}$ 2973, 2159, 1977, 1739, 1613, 1535, 1446, 1387, 1146; $\delta_H$ (400 MHz, CD$_3$OD) 4.55 (dd, J=3.5, 6.0 Hz, 1H), 4.75 (dd, J=3.5, 15.0 Hz, 1H), 4.80 (dd, 6.0, 15.0 Hz, 1H), 7.80 (s, 1H), 7.99 (d, J=2.0 Hz, 1H); $\delta_C$ (101 MHz, D$_2$O) δ0.0 (s), 52.7 (s), 111.0 (d, J=214.5 Hz), 136.3 (d, J=23.5), 143.2 (d, J=14.5 Hz), 168.8 (s); $\delta_P$ (101 MHz, D$_2$O) 10.73; [α]$_D^{22}$ +30 (c 1.0, H$_2$O); m/z (ES) Found: MH$^+$ 236.0426 C$_6$H$_{11}$N$_3$O$_5$P requires MH$^+$ 236.0436.

1.5 Preparation of Compounds of Formula VII: (2S)-2-(Carboxyamino)-3-(4-phosphonothiophen-2-yl)propanoic acid, Compound 17

1.5.1 Diethyl (thiophen-3-yl) phosphonate, Compound 13

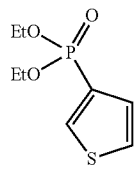

Palladium acetate (202 mg, 0.9 mmol, 0.03 eqv), dppf (998 mg, 1.8 mmol, 0.06 eqv), and sodium acetate (295 mg, 3.6 mmol, 0.12 eqv) were added to a round bottom flask with condenser, before being purged with nitrogen, by applying three cycles of vacuum, followed by nitrogen. Dry THF (60 mL) was then added by syringe followed by $^i$Pr$_2$EtN (4.65 g, 6.27 mL, 36 mmol, 1.2 eqv). The reaction mixture was then stirred at 60° C. for 30 minutes, before addition of 3-bromothiophene (4.89 g, 2.81 mL, 30 mmol, 1 eqv) and diethyl phosphite (4.14 g, 3.86 mL, 30 mmol, 1 eqv). The reaction mixture was then brought to reflux and left for 24 hours. The crude reaction mixture was then concentrated by reduced pressure and applied directly to a silica gel column for purification, using 40% EtOAc/60% 40-60 Petroleum ether, to afford the desired compound 13 (4.76 g, 21.6 mmol, 72% yield).

Yellow oil; $v_{max}$ (film)/cm$^{-1}$ 3474, 3103, 2983, 2939, 2905, 1500, 1478, 1444, 1393, 1369, 1208, 1164, 1119, 1098, 1051, 1023; $\delta_H$ (400 MHz, CDCl$_3$) 1.34 (t, J=7.0 Hz, 6H), 4.05-4.21 (m, 4H), 7.33-7.37 (m, 1H), 7.45 (dt, J=3.0, 5.0 Hz, 1H), 8.01 (ddd, J=1.0, 3.0, 8.0 Hz, 1H); $\delta_C$ (101 MHz, CDCl$_3$) 16.3 (d, J=6.5 Hz), 62.2 (d, J=5.5 Hz), 127.2 (d, J=18.0 Hz), 129.0 (d, J=16.5 Hz), 129.5 (d, J=195.5 Hz), 135.4 (d, J=18 Hz); $\delta_P$ (101 MHz, CDCl$_3$) 13.6 (s); m/z (ES) Found: MH$^+$ 221.0391. C$_8$H$_{14}$O$_3$PS requires MH$^+$ 221.0401.

1.5.2 Diethyl (5-iodothiophen-3-yl) phosphonate, Compound 14

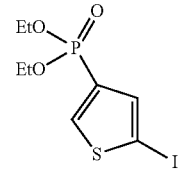 [SMILES: CCOP(=O)(OCC)c1csc(I)c1]

A solution of compound 13 (1.10 g, 5 mmol) in EtOH (10 mL) was added to a round bottom flask with condenser containing H₅IO₆ (0.57 g, 2.5 mmol, 0.5 eqv) and I₂ (0.54 g, 2.15 mmol, 0.43 eqv). The reaction mixture was then brought to reflux and left overnight stirring. The reaction mixture was then concentrated via reduced pressure, and purified by silica gel column using 30% EtOAc/70% 40-60 petroleum ether to afford the desired compound 14 (1.09 g, 3.15 mmol, 63% yield).

Thick yellow oil; $v_{max}$ (film)/cm⁻¹ 3468, 3092, 2981, 2931, 2900, 1495, 1476, 1442, 1391, 1327, 1292, 1342, 1181, 1164, 1099, 1050, 1022; $\delta_H$ (400 MHz, CDCl₃) 1.34 (t, J=7.0 Hz, 6H), 4.03-4.22 (m, 4H), 7.44 (dd, J=1.5, 4.0 Hz, 1H), 7.99 (dd, J=1.5, 9.0 Hz, 1H); $\delta_C$ (101 MHz, CDCl₃) 16.3 (d, J=6.5 Hz), 62.4 (d, J=5.5 Hz), 75.4 (d, J=23.0 Hz), 132.0 (d, J=195.5 Hz), 138.1 (d, J=16.0 Hz), 141.1 (d, J=17.0 Hz); $\delta_P$ (101 MHz, CDCl₃) 10.56 (s); m/z (ES) Found: MH⁺ 346.9383. C₈H₁₃O₃PSI requires MH⁺ 346.9368.

1.5.3 Methyl (2S)-2-{[(tert-butoxy)carbonyl]amino}-3-[4-(diethoxyphosphoryl)thiophen-2-yl]propanoate, Compound 15

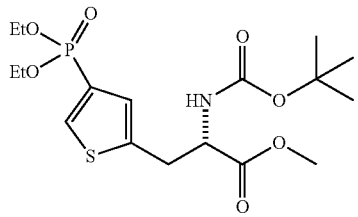 [SMILES: CCOP(=O)(OCC)c1csc(C[C@H](NC(=O)OC(C)(C)C)C(=O)OC)c1]

Zinc dust (588 mg, 9 mmol, 6 eqv) was added to a flame dried nitrogen purged side arm round bottom flask. DMF (3 mL) was added via syringe followed by a sub-stoichiometric amount of iodine (120 mg, 0.45 mmol, 0.15 eqv). Once the reaction mixture had turned colourless N-(tert-Butoxycarbonyl)-3-iodo-L-alanine methyl ester (987 mg, 3 mmol, 1.5 eqv) was added. The reaction mixture was then monitored via TLC to check for complete zinc insertion. Once the spot for N-(tert-Butoxycarbonyl)-3-iodo-L-alanine methyl ester had disappeared, the reaction mixture was transferred to another flame dried nitrogen purged side arm round bottom flask. Pd₂(dba)₃ (46 mg, 0.05 mmol, 0.025 eqv), SPhos (46 mg, 0.10 mmol, 0.05 eqv) and compound 14 (700 mg, 2.0 mmol, 1.0 eqv) were then added to the flask. The reaction was heated to 50° C. and left stirring overnight, under a positive pressure of nitrogen. The reaction mixture was then partitioned between EtOAc and Brine, followed by extraction of the aqueous layer with EtOAc (2×). The organic layers were then combined, dried with MgSO₄, and concentrated under reduced pressure. The crude compound was then purified by silica gel column using 50% EtOAc/50% toluene to afford the desired compound 15 (329 mg, 0.78 mmol, 39% yield).

Thick yellow oil; $v_{max}$ (film)/cm⁻¹ 3272, 3100, 2980, 2930, 2896, 1747, 1713, 1529, 1436, 1392, 1366, 1289, 1245, 1166, 1094, 1052, 1023; $\delta_H$ (400 MHz, CDCl₃) 1.31 (t, J=7.0 Hz, 6H), 1.44 (s, 9H), 3.31 (dd, J=5.0, 15.0 Hz, 1H), 3.40 (dd, J=5.0, 15.0 Hz, 1H), 3.74 (s, 3H), 4.01-4.19 (m, 4H), 4.55-4.63 (m, 1H), 5.19 (d, J=7.5 Hz, 1H), 6.98-7.03 (m, 1H), 7.84 (d, J=9.0 Hz, 1H); $\delta_C$ (101 MHz, CDCl₃) 16.3 (d, J=6.5 Hz), 28.2 (s), 32.3 (s), 52.5 (s), 54.2 (s), 62.3 (d, J=4.5 Hz), 80.23 (s), 128.2 (d, J=16.5 Hz), 129.6 (d, J=109.0 Hz), 135.2 (d, J=17.0 Hz), 140.1 (d, J=19.5 Hz), 155.0 (s), 171.3 (s); $\delta_P$ (101 MHz, CDCl₃) 12.73 (s); $[\alpha]_D^{22}$ +54 (c 1.0, CHCl₃); m/z (ES) Found: MH⁺ 422.1414 C₁₇H₂₃NO₇PS requires MH⁺ 422.1402.

1.5.4 (2S)-2-{[(tert-butoxy)carbonyl]amino}-3-[4-(diethoxyphosphoryl)thiophen-2-yl]propanoic acid, Compound 16

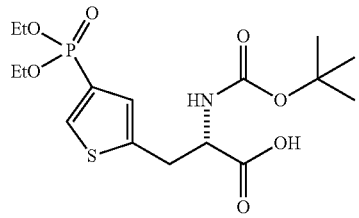 [SMILES: CCOP(=O)(OCC)c1csc(C[C@H](NC(=O)OC(C)(C)C)C(=O)O)c1]

Compound 15 (316 mg, 0.75 mmol, 1 eqv) was added to a round bottom flask followed by the addition H₂O (1.5 mL) and THF (1.5 mL). Once dissolved LiOH (22 mg, 0.9 mmol, 1.2 eqv) was added and the reaction was monitored via TLC until the starting material spot had disappeared. The reaction was then concentrated by reduced pressure, and partitioned with Et₂O, followed by washing the aqueous layer with Et₂O (2×). The aqueous layer was then carefully acidified to pH 5, using 1M HCl, before partitioning with EtOAc, followed by a extraction of the aqueous layer with EtOAc (4×) while maintaining the aqueous layer at pH 5. The EtOAc layers were then combined, dried with MgSO₄, and the solvent removed via reduced pressure to give the pure compound 16 (306 mg, 0.75 mmol, <99% yield).

Thick pale yellow oil; $v_{max}$ (film)/cm⁻¹ 3425, 3330, 3093, 2979, 2931, 2906, 2842, 2549, 1712, 1500, 1435, 1392, 1367, 1333, 1231, 1164, 1094, 1051, 1021; $\delta_H$ (400 MHz, CDCl₃) 1.28 (t, J=7.0 Hz, 6H), 1.42 (s, 9H), 3.34 (dd, J=5.0, 15.0 Hz, 1H), 3.45 (dd, J=5.0, 15.0 Hz, 1H), 3.98-4.17 (m, 4H), 4.56 (m, 1H), 5.37 (d, J=7.5 Hz, 1H), 7.04 (d, J=3.5 Hz, 1H), 7.83 (d, J=9.0 Hz, 1H), carboxylic acid proton not observed; $\delta_C$ (101 MHz, CDCl₃) 16.2 (d, J=6.5 Hz), 28.3 (s), 32.0 (s), 54.0 (s), 62.6 (d, J=4.5 Hz), 80.0 (s), 128.0 (d, J=196.7 Hz), 128.1 (d, J=17.0 Hz), 135.3 (d, J=17.4 Hz), 140.8 (d, J=19.5 Hz), 155.2 (s), 172.4 (s); $\delta_P$ (101 MHz, CDCl₃) 13.34; $[\alpha]_D^{22}$ +42 (c 1.0, CHCl₃); m/z (ES) Found: MH⁺ 408.1246 C₁₆H₂₇NO₇PS requires MH⁺ 408.1246.

1.5.5 (2S)-2-(Carboxyamino)-3-(4-phosphonothiophen-2-yl)propanoic acid, Compound 17 (Also Referred to Herein as 4-phosphothiophen-2-yl alanine)

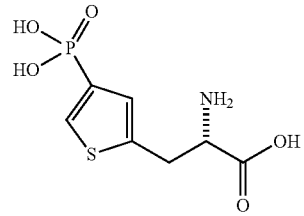 [SMILES: N[C@@H](Cc1cc(P(=O)(O)O)cs1)C(=O)O]

Compound 16 (204 mg, 0.5 mmol, 1 eqv) in a solution of MeCN (5 mL) was added to a round bottom flask, followed by the addition of trimethylsilyl bromide (765 mg, 660 µL, 5 mmol, 10 eqv). The reaction mixture was then brought up to 50° C. and left overnight. The solvent was then removed from the reaction mixture via reduced pressure and the resulting residue was triturated using H$_2$O and isopropanol to give the desired compound 17 (55 mg, 0.22 mmol, 44% yield).

Amorphous cream solid; m.p. 260° C. decamp.; $v_{max}$ (film)/cm$^{-1}$ 3403, 2991, 2892, 1971, 1713, 1603, 1586, 1519, 1447, 1427, 1305, 1253, 1191, 1140, 1093, 1041; $\delta_H$ (400 MHz, D$_2$O) 3.34-3.47 (m, 2H), 4.26 (t, J=6.0 Hz, 1H), 7.06 (d, J=4.0 Hz, 1H), 7.73 (d, J=9.0 Hz, 1H); $\delta_C$ (101 MHz, D$_2$O) 29.6 (s), 53.9 (s), 129.4 (d, J=16.5 Hz), 133.3 (d, J=17.0 Hz), 134.6 (d, J=187.0 Hz), 137.3 (d, J=18.5 Hz), 171.0 (s); $\delta_P$ (101 MHz, D$_2$O) 8.19 (s); $[\alpha]_D^{22}$ −18 (c 1.0, H$_2$O); m/z (ES) Found: MH$^+$ 252.0098 C$_7$H$_{11}$NO$_5$PS requires MH$^+$ 252.0096.

1.6 Characterisation Data for Compounds of Formula III: (S)-2-Amino-3-(5-phosphoryl-1,3-thiazol-2-yl)propanoic acid, Compound 20

Compound 20 of Formula III was synthesized via the intermediates 18 and 19 identified below.

1.6.1 Methyl (2S)-2-amino(tert-butoxycarbonyl)-3-(5-bromo-1,3-thiazol-2-yl) propanoate, Compound 18

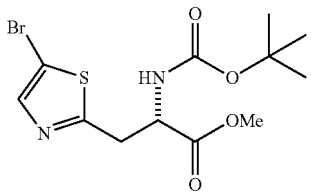 [SMILES: COC(=O)[C@H](Cc1ncc(Br)s1)NC(=O)OC(C)(C)C]

$R_f$ 0.46 (30% EtOAc in toluene); $v_{max}$ (thin film)/cm$^{-1}$ 3344, 2974, 2932, 1740, 1699, 1508, 1437, 1363, 1282, 1256, 1211, 1166, 1098, 988, 847; $\delta_H$ (400 MHz, CDCl$_3$) 1.46 (9H, s), 3.44-3.55 (2H, m), 3.76 (3H, s); 4.67-4.74 (1H, m), 5.61 (1H, d, J=7.8 Hz), 7.58 (1H, s), $\delta_C$ (101 MHz, CDCl$_3$) 28.3, 35.5, 52.6, 52.7, 80.3, 108.6, 143.7, 155.2, 166.6, 171.2; $[\alpha]_D^{24}$ +37.0 (c. 1.0, CHCl$_3$); m/z (ES) Found: MH$^+$ 365.0165, C$_{12}$H$_{18}$N$_2$O$_4$SBr requires MH$^+$ 365.0171.

1.6.2 Methyl (2S)-2-amino(tert-butoxycarbonyl)-3-(5-(diethoxyphosphoryl)-1,3-thiazol-2-yl) propanoate, Compound 19

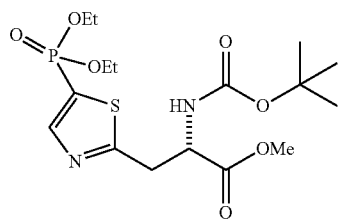 [SMILES: CCOP(=O)(OCC)c1cnc(C[C@H](NC(=O)OC(C)(C)C)C(=O)OC)s1]

$R_f$ 0.30 (EtOAc); $v_{max}$ (thin film)/cm$^{-1}$ 3285, 2984, 2939, 1748, 1718, 1502, 1442, 1368, 1248, 1163, 1088, 1018, 977; $\delta_H$ (400 MHz, CDCl$_3$) 1.38-1.31 (6H, m), 1.43 (9H, s), 3.51-3.65 (2H, m), 3.74 (3H, s), 4.07-4.23 (4H, m), 4.70-4.77 (1H, m), 5.65 (1H, d, J=8.1 Hz), 8.10 (1H, d, J=4.3 Hz); $\delta_C$ (101 MHz, CDCl$_3$) 16.3, 28.3, 35.3, 52.7, 52.8, 63.0, 63.1, 80.3, 123.6 (d, J=110 Hz), 150.8, 150.9, 155.0, 171.1; $\delta_P$ (101 MHz, CDCl$_3$) 9.4; $[\alpha]_D^{24}$ +31.0 (c. 1.0, CHCl$_3$); m/z (ES) Found: MH$^+$ 423.1336, C$_{16}$H$_{27}$N$_2$O$_7$PS requires MH$^+$ 423.1355.

1.6.3 (S)-2-Amino-3-(5-phosphoryl-1,3-thiazol-2-yl) propanoic acid, Compound 20

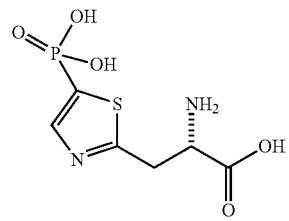 [SMILES: N[C@@H](Cc1ncc(P(=O)(O)O)s1)C(=O)O]

m.p. 196-199° C. (decomp.); $\delta_H$ (400 MHz, D$_2$O) 3.59 (1H, dd, J=6.9, 16.5 Hz), 3.65 (1H, dd, J=5.2, 16.5 Hz), 4.38 (1H, dd, J=5.2, 6.6 Hz), 7.82 (1H, d, J=4.5 Hz); $\delta_P$ (101 MHz, DMSO) 1.7 (s); m/z (ES) MH$^+$ 253.0.

2. Antibody Generation and Testing

2.1 Phosphohistidine Analogues

2.1.1 General Coupling Procedure of Analogues to a Carrier Protein Using Glutaraldehyde Carrier protein, KLH or BSA, (50 mg) and the phosphohistidine analogue (5 mg) were added to a vessel followed by the addition of pH 7.4 phosphate buffered saline (1 mL, 137 mM NaCl, 10 mM Phosphate, 2.7 mM KCl). 50% wt glutaraldehyde in H$_2$O was then added to the reaction mixture to result in a final concentration of 0.1% wt glutaraldehyde and was then left overnight at 4° C., rotating gently. NaBH$_4$ (5 mg) was added to the solution and was then left overnight at 4° C., rotating gently. The reaction mixture was then diluted to 2.5 mL using pH 7.4 phosphate buffered saline and then subjected to dialysis overnight at 4° C. in pH 7.4 phosphate buffered saline (1 L), to give the desired protein-amino acid conjugate in solution (20 mg/mL).

2.1.2 Maldi-TOF Mass Spectrometry of BSA-Amino Acid Conjugates

Sinapinic acid was used as the matrix for MS analysis of peptide or protein solutions, respectively. Aliquots (1.3 μL) of the matrix solution (10 mg SA in 1 mL aqueous solution of 66% [v/v] acetonitrile containing 0.1% [v/v] formic acid) were mixed with the peptide or protein solution, made by procedure 2.1.1, and spotted onto a MALDI-TOF target. A Brucker Reflex III with a nitrogen laser was used to analyze the samples. Protein/peptide mass was measured using the positive-ion linear mode.

2.1.3 Procedure for the Generation of Polyclonal Antibodies of Each Analogue Protein-phosphohistidine analogue solution (100 μL), was added to an equal volume of Freunds complete adjuvant.

The solution was then passed through a 23G needle until an emulsion, which does not separate on standing, forms. Each rat was then injected subcutaneously with the emulsion (200 μL). After 2 weeks an additional injection was performed, using the same procedure as above but with Freunds incomplete adjuvant, and was then repeated again after an additional 2 weeks. After 10 days test bleeds were collected from the rats for assays. If the immunoresponse was too low, a further injection was performed using the solution made with Freunds incomplete adjuvant, and test bleeds collected for assays. After 3 weeks, post the last injection, one final injection was performed with the solution of antigen and Freunds incomplete adjuvant, then the terminal bleed is collected after 10 days. The terminal bleeds are then allowed to clot overnight at 4° C., before centrifuging at 13000 rpm in a benchtop microfuge, to give the serum as the top clear layer.

2.1.4. ELISA Procedure

During the immunology protocol described in 2.1.3 test bleeds were taken at monthly intervals. These were subject to an ELISA in order to monitor the immune response. The BSA conjugates were first bound to the surface of wells (FIG. 1, A); this was used instead of the KLH conjugate to improve the noise to detection ratio as the polyclonal sera also contain antibodies towards KLH. The test bleeds were then serially diluted and incubated with the surface bound protein for 2 hours, before rinsing the solutions away with PBS, leaving the selective antibodies for the mimic bound to the protein (FIG. 1, B). The bound primary antibodies were then incubated with a secondary antibody, that can detect the primary antibody and has horseradish peroxidase (HRP) conjugated to it (FIG. 1, C). The bound HRP can then be visualised using 3,3',5,5'-tetramethylbenzidine (TMB) to give a relative concentration of HRP in the well (FIG. 1, D).

2.1.4.1 Results of ELISA

Figure 2:
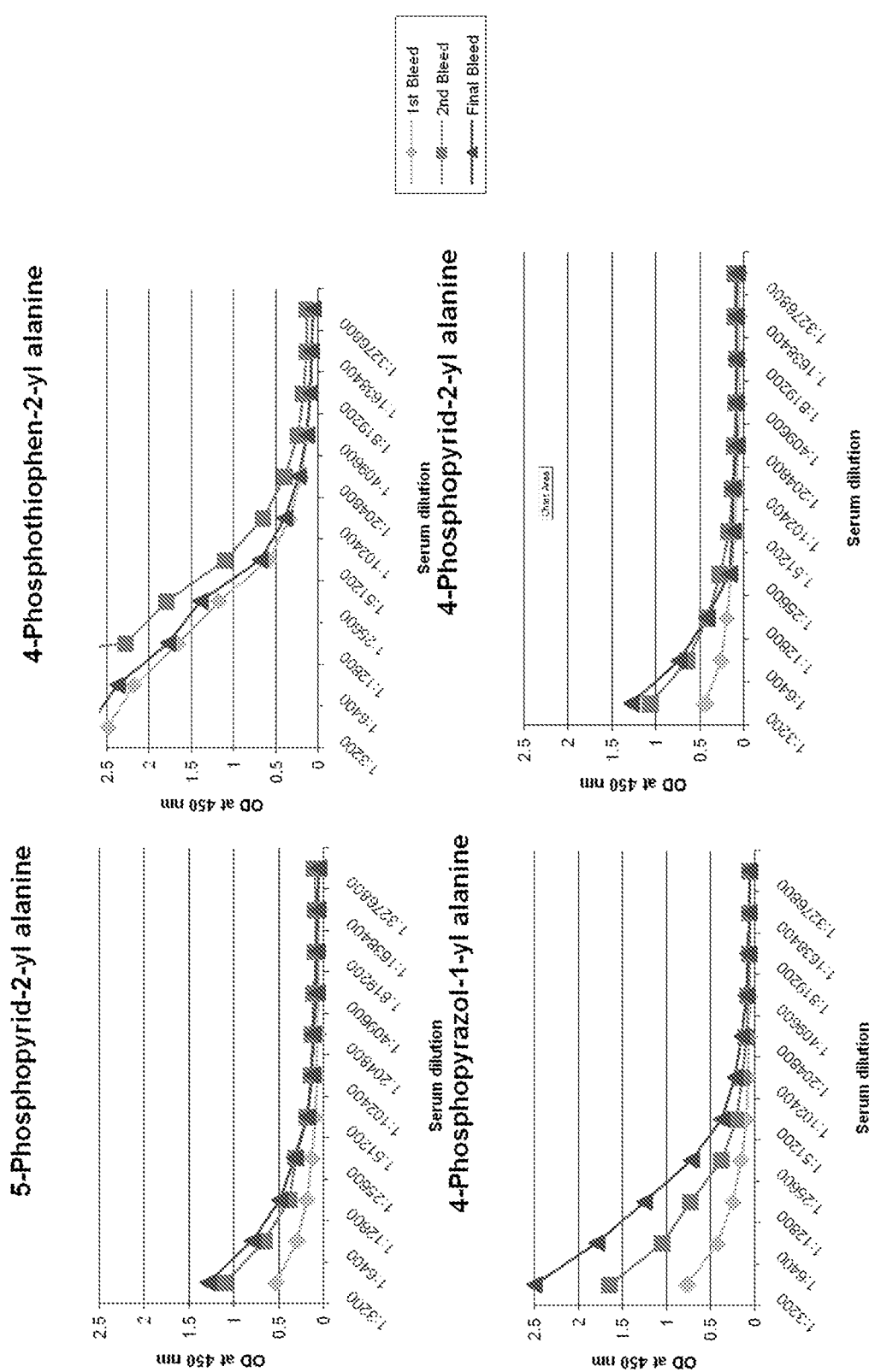
FIG. 2 shows graphs to illustrate the ELISA results from immunization of mice using the phosphohistidine analogues.

The results from the ELISA showed that each of the rats successfully generated an immune response to the stable phosphohistidine analogue of interest (FIG. 2).

2.1.5 General Dot Blot Procedure

Solutions of the BSA-amino acid conjugates of histidine, tele-phosphohistidine, and the analogues, were first diluted 1000 fold. These solutions as well as the commercially available solutions of BSA conjugated to phosphoserine, phosphothreonine, and phosphotyrosine were spotted (2 μL) onto a PVDF membrane. Once the spots were dry, the membrane was rinsed with methanol before being blocked in 5% non-fat dry milk in 10 mM Tris-HCl pH 8.0, 17 mM NaCl (TBS), Tween (0.05%) (5% NFDM/TBST) for 1 hour and then incubated with the rat sera raised against the analogue of interest at $\frac{1}{1000}$ dilution in 5% NFDM/TBST overnight at 4° C. The membrane was then washed using TBS-Tween (0.05%) 3 times for 15 minutes, before being incubated with a $\frac{1}{2000}$ fold dilution of goat anti-rat IgG-HRP conjugate in 5% NFDM/TBST for 60 minutes at room temperature. Membranes were then washed 3 times for 15 minutes using TBS-Tween (0.05%) and then treated with SuperSignal West Dura Chemiluminescent Substrate for 3 minutes. The images were then captured on a Chemidoc XRS⁺ CCD imaging system.

2.1.5.1 Results of Dot Blot Analysis

The polyclonal sera generated by each of the analogues were then subjected to dot-blot analysis to determine the selectivity of the crude sera against a series of control samples.

Phosphoserine, phosphothreonine, and phosphotyrosine are each commercially available prebound to BSA. Histidine and tele-phosphohistidine were generated using Hultquist's method and purified by chromatography and were each conjugated to BSA using glutaraldehyde. The results from the dot blot analysis are shown in FIG. 3.

2.1.6 General Affinity Column Preparation

Affinity purification was then performed separately on each of the polyclonal antibodies raised against the stable analogues.

AminoLink coupling resin (4 mL) was added to a column and the storage solution drained off to the level of the resin. The column is then washed with 1M pH 7.4 PBS (12 mL) and the contents then drained. A solution of the conjugated protein to KLH (4 mL), prepared using procedure 2.1.1, was added to the resin followed by a solution of 5M NaCNBH3 in 1M NaOH (40 μL). The reaction was then mixed by end-over-end rocking overnight at 4° C. The solution is then drained from the column and washed with 1M pH 7.4 PBS (12 mL) and drained. 1M Tris.HCl pH 7.4 was then added to the resin followed by 5M NaCNBH$_3$ in 1M NaOH (40 μL), and mixed gently at room temperature for 30 minutes by end over end rocking, before draining off the solution. The column is then washed with 1M NaOH (40 mL) and then 1M pH 7.4 PBS containing 0.05 wt % sodium azide for storage.

2.1.7 Affinity Depletion of the Polyclonal Antibody Protocol

The storage solution was drained from the affinity column containing the amino acid that was to be affinity depleted, and washed with 1M pH 7.4 PBS solution (10 mL). The solution was then drained to the level of the resin, before gentle addition of the polyclonal serum (0.5 mL) to the top of the resin. The serum was then allowed to flow into the resin, before being left overnight at 4° C., the resin was the washed with 1M pH 7.4 PBS solution collecting 500 μL fractions. The fractions were then tested via ELISA and Bradford assay to determine quantity and quality of the antibodies collected.

2.1.8 ELISA Studies Using Affinity Purified Polyclonal Antibodies

Competition studies were then performed on the purified polyclonal antibody sera, generated from 4-phosphopyrid-2-yl alanine and 4-phosphopyrazol-1-yl alanine.

1 mM solutions of the amino acid of histidine, τ-phosphohistidine, phosphoserine, phosphothreonine and phosphotyrosine were made using of 1 M pH 7.4 PBS/Tween-20+0.2% gelatine to give the desired initial concentration of 1 mM. 100 μL of the appropriate amino acid solution were added to the top row of the 96 well cell culture plate, and 1 M pH 7.4 PBS/Tween-20+0.2% gelatin (50 μL) was added to the remaining wells. The amino acid solutions were then used to make 2.5 mM, 1.25 mM, 0.63 mM, 0.32 mM, 0.16 mM, 0.08 mM, and 0.04 mM solutions in the remaining wells, to give the 96 well plate as illustrated in FIG. 10.

The purified antibody of interest was then was diluted in 1 M pH 7.4 PBS/Tween-20+0.2% gelatin to half the dilution that gave an optical density (OD) of 1.0 at 450 nm according to ELISA method 2.1.4. The primary antibody solution (100 μL) was then added to each of the wells, apart from cells B11-12 and D11-12 (FIG. 10). The 96 well plate was then incubated overnight at 4° C.

2.1.8.1 Dot Blot Analysis of Purified Antibodies from 4-phosphopyrazol-1-yl alanine The crude polyclonal antisera detected tele-phosphohistidine, with some cross-reactivity to histidine (FIG. 4, Entry A). Purification using a histidine-sepharose affinity matrix did not completely remove this cross-reactivity (FIG. 4, Entry B), but subsequent purification using a glutaraldehyde-conjugated histidine-KLH sepharose affinity matrix removed the cross-reactivity (FIG. 4, Entry C).

Figure 11:
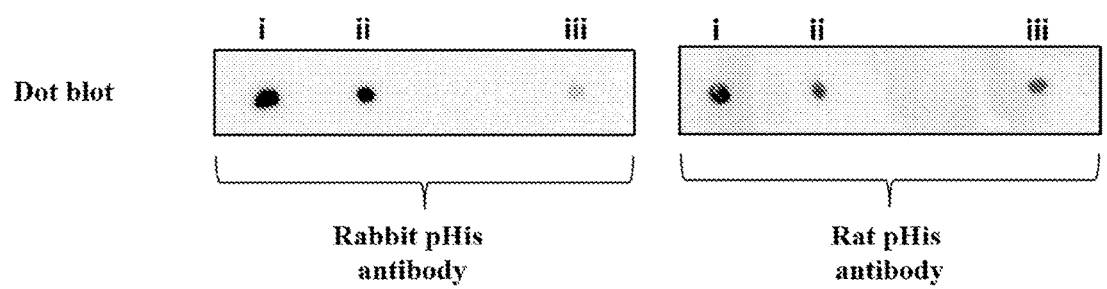
FIG. 11 shows dot blots of both rabbit and rat polyclonal sera raised against 4-phosphopyrazol-1-yl alanine, affinity depleted using glutaraldehyde-conjugated histidine-KLH and then screened against BSA-glutaraldehyde conjugated 4-phosphopyrazol-1-yl alanine (i), 4-phosphopyrazol-1-yl alanine amide (ii), and 4-phosphothiazol-1-yl alanine amide (iii).

In addition, further antibodies against 4-phosphopyrazol-1-yl alanine were raised as described in sections 2.1.1 to 2.1.4 above, and dot blot analysis conducted as described in section 2.5. FIG. 11 shows dot blots of both the rabbit and rat polyclonal sera raised against 4-phosphopyrazol-1-yl alanine, affinity depleted using glutaraldehyde-conjugated histidine-KLH coupled to a Sepharose matrix as described for FIG. 4, Entry C and then screened against BSA-glutaraldehyde conjugated 4-phosphopyrazol-1-yl alanine (i), 4-phosphopyrazol-1-yl alanine amide (ii), 4-phosphothiazol-1-yl alanine amide (iii). The data establishes that 4-phosphopyrazol-1-yl alanine amide and 4-phosphothiazol-1-yl alanine amide are detected by the polyclonal sera raised against 4-phosphopyrazol-1-yl alanine.

2.1.9 Western Blots Using Affinity Purified Polyclonal Antibodies

Western blots were then performed to demonstrate the utility of the antibodies of the invention in a standard biological technique.

Tele-Phosphohistidine-BSA solution (2 μg, 2 μL) was added to an Eppendorf tube, followed by 4×LDS sample buffer (10 μL) and of 500 mM DTT (4 μL). The sample was then incubated at room temperature for 60 min, while waiting the polyacrylamide gel was prepared. A 10% resolving gel solution was prepared by adding 1.5 M TriCl pH 8.8 (5 mL), acrylamide 30% (w/v) (6.6 mL), 20% SDS (100 μL) and water (8 mL). The solution was then activated using a 10% (w/v) APS in water solution (200 μL) and TEMED (20 μL). The solution was then quickly transferred to the plates, before layering with water saturated n-butanol. While the resolving gel was setting the stacking gel solution was prepared (0.5 M TriCl pH 6.8 (2.5 mL), acrylamide 30% (w/v) (1.3 mL), 20% SDS (50 μL) and water (6 mL). Once the resolving gel was set the n-butanol was removed, and the stacking gel was activated used 10% (w/v) APS in water solution (50 μL) and TEMED (10 μL). The stacking gel solution was then quickly transferred to the plate, and the comb template added. Once set, the comb was removed and the protein solution and ColorPlus™ Prestained Protein Ladder, Broad Range (10-230 kDa) were loaded onto the 10% polyacrylamide gel and resolved by electrophoresis. The proteins were then transferred to a PVDF membrane using Towbin buffer (192 mM glycine, 25 mm Tris-HCl), and visualised using the general dot blot procedure described herein.

2.1.9.1 Results of Western Blots

Denaturing of the tele-phosphohistidine-BSA conjugate using Laemmli buffer at 90° C. for 3 minutes gave no signal from the polyclonal antibodies generated from 4-phosphopyrazol-1-yl alanine. It was proposed that the high temperature used to denature the protein was dephosphorylating the sample, and therefore leaving no tele-phosphohistidine to be detected by the polyclonal antibodies. The denaturing of the protein was therefore repeated at room temperature using 10 times more concentrated Laemmli buffer for 30 minutes, this led to some promising results for detection of the target protein, however complete denaturing had not occurred (FIG. 5, A).

Figure 5:
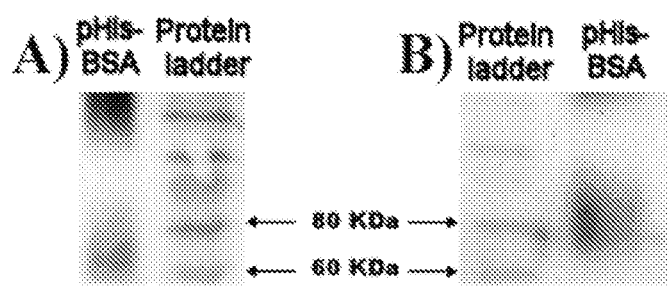
FIG. 5 Western blot of tele-phosphohistidine conjugated to BSA denatured by either Laemmli buffer containing SDS (A) and Laemmli buffer containing LDS (B) for 30 mins at room temperature, before visualising polyclonal antibodies generated from 4-phosphopyrazol-1-yl alanine.

Lithium dodecyl sulphate (LDS) is an alternative denaturing reagent that has been known to replace sodium dodecyl sulphate (SDS) in the Laemmli buffer, and is used to allow for more efficient denaturing of proteins at lower temperatures.[243] Using the Laemmli buffer containing LDS instead of SDS allowed for a more efficient denaturing of the protein, leaving a single band at the expected molecular weight (FIG. 5, B)

2.2. Phosphotyrosine Analogues

Figure 8:
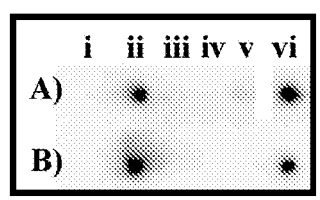
FIG. 8 shows Dot-blots using anti-sera generated from 4-phosphothiophen-2-yl alanine of A) Crude polyclonal antisera, B) Affinity depleted sera using histidine-KLH using glutaraldehyde.
Figure 8:
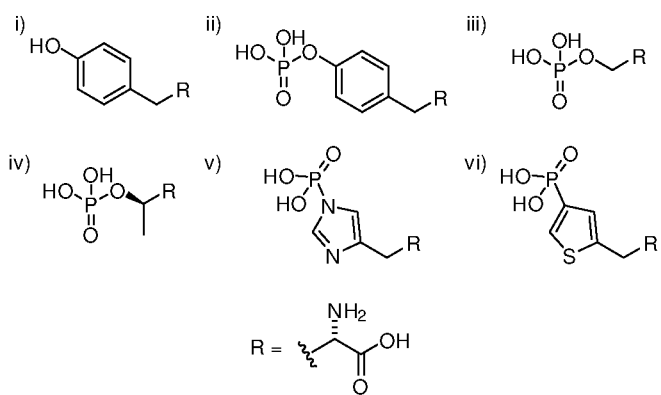

4-Phosphothiophen-2-yl alanine while not being a suitable stable analogue for tele-phosphohistidine, showed potential as a stable analogue for phosphotyrosine. Re-screening of this antibody against tyrosine as well as the previously selected phosphoamino acids, showed a good selectivity towards phosphotyrosine with a small amount of side reactivity towards tele-phosphohistidine conjugated to BSA (FIG. 8, Entry A). This cross reactivity was simply removed via affinity depletion using a sepharose column bound with the histidine-KLH glutaraldehyde conjugate (FIG. 8, Entry B).

Figure 9:
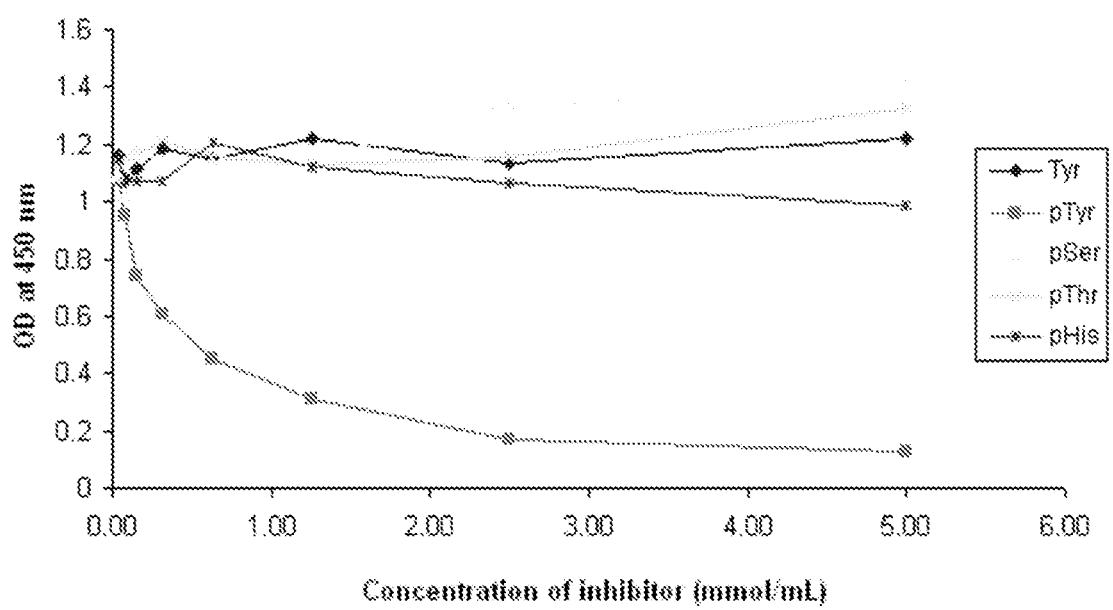
FIG. 9 shows competitive inhibition ELISA study using anti-sera generated from 4-phosphothiophen-2-yl alanine.

Competition studies were then performed on the purified polyclonal antibody sera, from 4-phosphothiophen-2-yl alanine. Interestingly, this antisera showed next to no inhibition by any of the amino acids the sera was screened against apart from phosphotyrosine. Suggesting while this mimic may not be a suitable stable analogue for tele-phosphohistidine, it looks as an ideal analogue for phosphotyrosine (FIG. 9).

3. Monoclonal Antibody Generation and Testing

3.1 Generation of Monoclonal Antibodies

3.1.1 Generation of Immune Response

An immune response to the analogues was generated as described in 2.1.3 above.

3.1.2 Removal of Murine Spleen

The sacrificed mouse was placed on its right hand side and the fur saturated with ethanol/hibitane spray to prevent contamination. In a sterile environment the forceps and scissors were removed aseptically from their sterile packaging. A flap of skin approximately 1 cm from the hind leg was gently lifted and incisions made vertically (about 3 cm) and horizontally (about 2 cm). Fatty connective tissue and deposits were removed from the sample to free the skin from the inner membrane. A second pair of scissors and forceps was used to make a cut in the peritoneal wall on the mouse's left side. The spleen was carefully removed from the peritoneal cavity, and the veins and connective tissue cut away from the spleen with care taken to avoid touching the non-sterile skin surface. The spleen was then transferred to a sterile petri dish. Clean flow hood thoroughly before commencing tissue culture.

3.1.3 Fusion of Hybridoma 7-10 days before the intended fusion, Sp2 cells were thawed and cultured in RPMI media with 10% foetal calf serum (FCS) such that at least $5 \times 10^7$ cells at ≥90% viability and a density of between $3-5 \times 10^5$ cells/ml were available for the day of fusion.

The following syringes were prepared on the day and the appropriate needle attached (2×10 mL syringe containing basal RPMI media with 25G needles, 1×10 mL syringe containg basal RMPI media with 21G needle, 1×1 mL syringe containg basal RMPI media with 21G needle, and 1×1 mL syringe containing PEG 1500 with 21 G needle) before incubating for at least 10 minutes in a CO2 incubator to equilibrate before use.

The removed spleen was then perfused by gently pricking the tissue using the 2×10 mL syringes fitted with 25G needles, before forcing the medium gently through the tissue. A sterile pipette was used to transfer the perfused cells from the petri dish to a sterile universal container. 10 µL of 0.4% solution of trypan blue in buffered isotonic was added to a 100 µL sample of the perfused cells, before counting the viable cells using a hemocytometer. A 100 µL sample of myeloma cells was counted in the same manner. The spleen cells were then combined with the myeloma cells to give a 5:1 ratio (spleen:myeloma).

The volume of myeloma cells required was then calculated to give a 5:1 ratio of spleen cells to myeloma cells. The pre-determined volume of myeloma cells was then transferred into a universal container and spun together with the universal containing the spleen cells at 2000 rpm for 5 mins at room temperature. The supernatants were then decanted off into a sterile universal and the tubes taped to dislodge the cell pellets. Each pellet was then re-suspended in 10 mLs of warm basal RPMI 1640 and mixed.

The media sample was then spun for 7 mins at 1850 rpm at room temperature, before decanting off the supernatant. The tube was then taped to dislodge the pellet, before warming in hand for 1 minute while being gently rotated in the tube. The PEG 1500 is then added slowly over 1 minute to the pellet, while being stirred and tapped. The mixture was then gently swirled in hand for 1 minute, before adding 1 mL of the basal RPMI over 1 minute the stirring still maintained. Finally the cell suspension is diluted further by adding 9 mL of basal RPMI 1640 slowly over two minutes, again ensuring the tube is tapped throughout.

The cell suspension is then spun for 15 minutes at 1500 rpm at room temperature, before decanting off the supernatant. The tube was again tapped to dislodge pellet, before adding 52 mLs of warm RPMI-1640/HAT+20% FCS. A multichannel pipette and sterile tips is then used to dispense the cell suspension in 100 µL aliquots to each well of labelled 96 well plates. The 96 well plates are then transferred to a $CO_2$ incubator at 37° C. and 95% humidity.

3.1.4 Post Fusion Care of Colonies

From day 4 the individual wells of 96 well plates were observed using ×100 and ×400 magnification on an inverted microscope for infection and cell growth. When the wells showed obvious signs of colony growth (clumps of >100 cells appear, medium begins to turn yellow) all the wells are fed by aseptically aspirating out the confluent medium and replacing with 200 µL of RPMI-1640/HAT+20% FCS medium.

Wells with colonies were then assayed by aseptically transferring 50 µL of medium from the identified wells to an ELISA plate and then topped up with 100 µL of RPMI-1640/HAT+20% FCS medium. Any wells that were identified as positive for tele-phosphohistidine with low response to the other controls (histidine-BSA, phosphoserine-BSA, phosphothreonine-BSA, phosphotyrosine-BSA) were expanded into 24 well plates by aspirating with a sterile Pasteur pipette and fed with complete medium.

3.1.5 Screening of Hybridomas by ELISA 96 well plates were prepared using the procedure highlighted in ELISA method E, using 50 µL of medium from the identified cell culture wells as the primary antibodies. Any cultures that showed a positive result to the tele-phosphohistidine, were screened again, after being grown in 24 well plates, using histidine-BSA, phosphoserine-BSA, phosphothreonine-BSA, phosphotyrosine-BSA, and tele-phosphohistidine-BSA bound in the 96 wells. Any samples that showed a strong response to tele-phosphohistidine-BSA (<0.7 OD), while maintaining a low response to the other amino acids were re-screened in consecutive weeks to ensure they were stable hybridomas.

3.2 Monoclonal Generation Results

Figure 6:
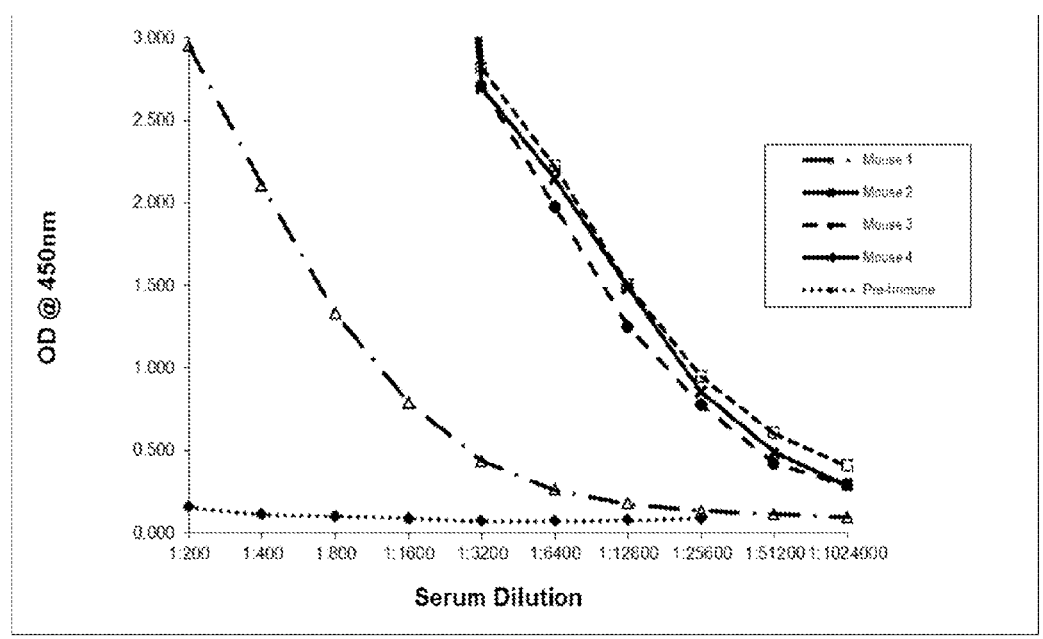
FIG. 6 shows ELISA response for mice test bleeds against 4-phosphopyrazol-1-yl alanine (polyclonal antibodies generated from 4-phosphopyrazol-1-yl alanine).

Four mice were immunised with 4-phosphopyrazol-1-yl alanine conjugated to KLH over a 3 month period, the final test bleeds showing a strong response to the antigen 4-phosphopyrazol-1-yl alanine conjugated to KLH from mice 2, 3, and 4 (FIG. 6).

Two of the mice with the strongest response to the antigen (4-phosphopyrazol-1-yl alanine conjugated to KLH) were therefore used to generate hybridomas. Fusion was performed successfully on both mice with hybrid colonies appearing in all of the 96 well plates as expected. The plates were then allowed to grow for 12 days before screening against the antigen, tele-phosphohistidine conjugated to BSA. Unfortunately the results from mouse 4 only had one weak positive response using a secondary antibody that detected mice immunoglobin G (IgG).

Due to the few positive responses in the assay for mouse 4, the other fusion (Mouse 2) was screened using a secondary antibody that picks up both IgG and IgM antibodies, showing 33 potential cell lines. Each of the positive wells from this assay, and the one positive from the first assay, were transferred to wells of 24 well plates and allowed to reach confluence. These wells were re-screened using the range of potentially cross-reactive materials conjugated to BSA (histidine, tele-phosphohistidine, phosphoserine, phosphothreonine, and phosphotyrosine). The majority of samples remaining positive against tele-phosphohistidine are also positive against one or more of the other targets. However one well, showed good selectivity to the phosphohistidine over the non-phosphorylated form and the other samples. This cell line was therefore cloned. Three other wells also showed some selectivity toward the tele-phosphohistidine and were also cloned.

Figure 7:
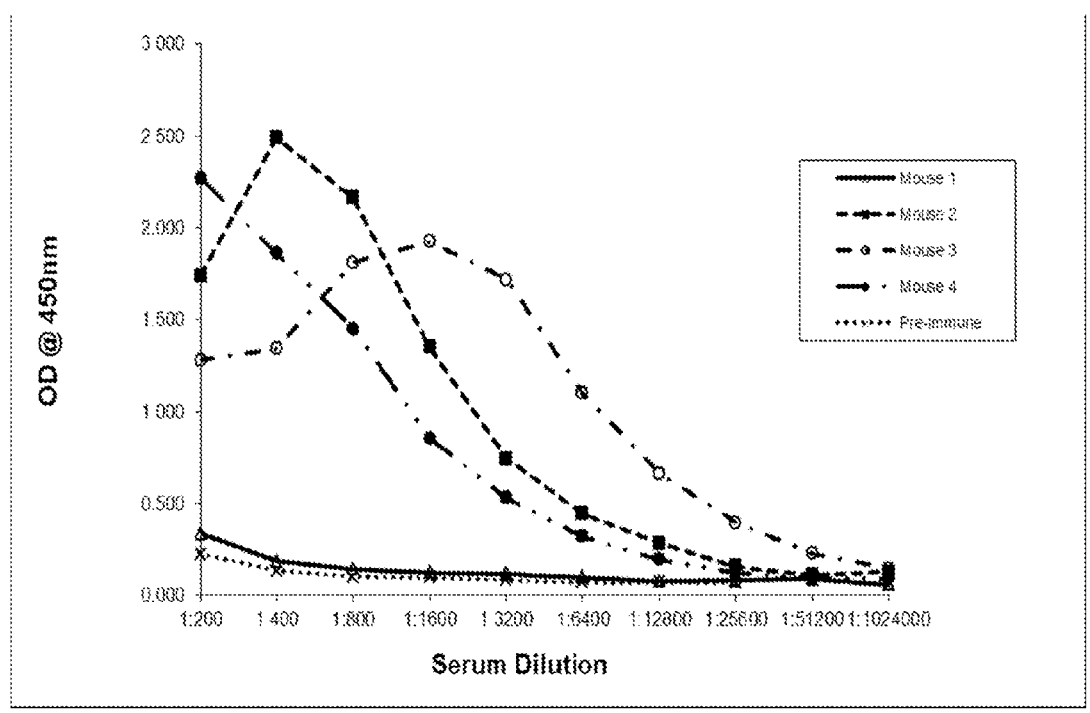
FIG. 7 shows ELISA response for mice test bleeds against tele-phosphohistidine (polyclonal antibodies generated from 4-phosphopyrazol-1-yl alanine).

It was suspected that the low number of viable hybridomas isolated could be due to an initial low response to tele-phosphohistidine. The final bleeds of the mice were therefore rescreened using tele-phosphohistidine as the antigen for the ELISAs. The ELISA showed that mouse 3 actually had the strongest response, while mouse 4 had a relatively weaker response (possibly explaining the low number of positives from the mouse 4 hybridomas) (FIG. 7).

Mouse 3 was used in hybridoma formation. Fusion was performed successfully on mouse 3 with hybrid colonies appearing in all of the 96 well plates. The plates were then allowed to grow for 12 days before screening the media from the cell cultures against the antigen, tele-phosphohistidine. A total of 77 potential wells were identified (6 IgGs and 71 Immunoglobin Ms (IgMs)). Each of these samples were then transferred to 24 well plates, before being allowed to grow to confluence. Upon re-screening of these samples two showed selectivity towards histidine and the other phospho-amino acids.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A phosphohistidine analogue of Formula V or Formula III:

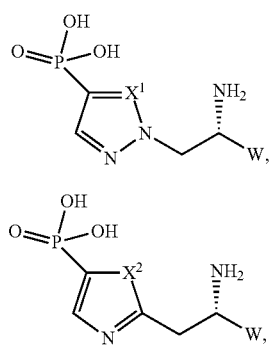

wherein

W is selected from H, CO$_2$H or CONH$_2$;

X$^1$ is CH;

X$^2$ is selected from NH, O or S.

2. The phosphohistidine analogue according to claim 1, wherein said analogue is selected from the group consisting of:

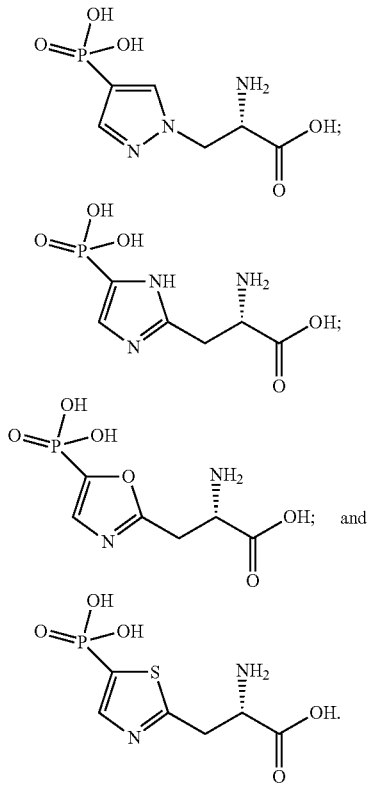

3. The phosphohistidine analogue according to claim 1, wherein the analogue is:

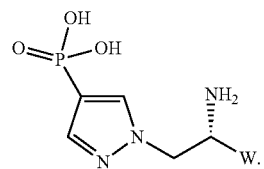

4. The phosphohistidine analogue of claim 1 wherein W is selected from H or CO$_2$H.

5. The phosphohistidine analogue according to claim 3, wherein W is selected from H or CO$_2$H.

6. A polypeptide that is a sequence of amino acids that are joined together through amide bonds, which sequence includes the analogue of claim 1.

7. A method of producing an anti-phosphohistidine antibody, comprising:
   (a) immunizing a non-human animal with an analogue according to claim 1, wherein said analogue is coupled to a carrier protein;
   (b) collecting serum from the immunized animal; and
   (c) isolating from the serum a population of polyclonal antibodies that specifically bind to the analogue.

8. The method according to claim 7, wherein said carrier protein is keyhole limpet hemocyanin (KLH), or bovine serum albumin (BSA).

9. A method of producing an anti-phosphohistidine antibody, comprising:
 (a) immunizing a non-human animal with an analogue according to claim 1, wherein said analogue is coupled to a carrier protein;
 (b) generating hybridomas by fusing B-cells isolated from the immunized animal with myeloma cells;
 (c) identifying hybridomas that produce monoclonal antibodies that specifically bind to the analogue; and
 (d) propagating said identified hybridomas to produce monoclonal antibodies that bind to the analogue.

10. The method according to claim 9, wherein said carrier protein is keyhole limpet hemocyanin (KLH), or bovine serum albumin (BSA).

11. A polypeptide that is a sequence of amino acids that are joined together through amide bonds, which sequence includes the analogue of claim 2.

12. A polypeptide that is a sequence of amino acids that are joined together through amide bonds, which sequence includes the analogue of claim 3.

\* \* \* \* \*